(12) United States Patent
Bach et al.

(10) Patent No.: US 10,632,154 B2
(45) Date of Patent: Apr. 28, 2020

(54) SI-HPMC-ENCAPSULATED INSULIN-PRODUCING CELLS FOR THE TREATMENT OF TYPE 1 DIABETES

(71) Applicants: ECOLE NATIONALE VETERINAIRE, Nantes (FR); CHU NANTES, Nantes (FR); UNIVERSITE DE NANTES, Nantes (FR); INSERM (INSTITUT NATIONAL DE LA SANTÉ ET DE LA RECHERCHE MÉDICALE), Paris (FR)

(72) Inventors: Jean-Marie Bach, Carquefou (FR); Mathilde Mosser, Nantes (FR); Apolline Salama, Nantes (FR); Anne Moure, Saint pre de Bigorre (FR); Xavier Leveque, Nantes (FR); Pierre Weiss, Nantes (FR); Jérôme Guicheux, Sainte Luce sur Loire (FR); Cécile Boyer, Nantes (FR); David Riochet, Nantes (FR)

(73) Assignees: Ecole Nationale Veterinaire, Nantes (FR); Chu Nantes, Nantes (FR); Universite de Nantes, Nantes (FR); Institute National de la Sante et de la Recherche Medicale, Paris (FR)

( * ) Notice: Subject to any disclaimer, the term of this patent is extended or adjusted under 35 U.S.C. 154(b) by 0 days.

(21) Appl. No.: 15/773,659

(22) PCT Filed: Nov. 10, 2016

(86) PCT No.: PCT/EP2016/077193
§ 371 (c)(1),
(2) Date: May 4, 2018

(87) PCT Pub. No.: WO2017/081112
PCT Pub. Date: May 18, 2017

(65) Prior Publication Data
US 2018/0318358 A1 Nov. 8, 2018

(30) Foreign Application Priority Data
Nov. 10, 2015 (EP) ..................................... 15193861

(51) Int. Cl.
| A61K 35/39 | (2015.01) |
| A61K 47/38 | (2006.01) |
| A61K 9/50 | (2006.01) |
| C12N 5/071 | (2010.01) |
| A61K 9/16 | (2006.01) |
| A61K 9/00 | (2006.01) |
| A61P 3/10 | (2006.01) |

(52) U.S. Cl.
CPC ............ *A61K 35/39* (2013.01); *A61K 9/0019* (2013.01); *A61K 9/1652* (2013.01); *A61K 9/5047* (2013.01); *A61K 47/38* (2013.01); *A61P 3/10* (2018.01); *C12N 5/0676* (2013.01); *C12N 5/0677* (2013.01); *A61K 9/0024* (2013.01); *C12N 2533/30* (2013.01)

(58) Field of Classification Search
CPC ...... A61K 47/38; A61K 9/1652; A61K 35/39; A61K 9/0019; A61K 9/5047; A61K 9/0024; C12N 5/0676; C12N 5/0677; C12N 2533/30; A61P 3/10
See application file for complete search history.

(56) References Cited

U.S. PATENT DOCUMENTS

| 8,278,106 B2* | 10/2012 | Martinson | ............... A61K 35/39 435/377 |
| 8,440,462 B2* | 5/2013 | Weiss | .................. A61L 27/3817 435/374 |
| 2011/0104780 A1* | 5/2011 | Jaroch | ..................... A61K 47/02 435/176 |
| 2013/0131828 A1* | 5/2013 | Legeay | .................... A61L 27/54 623/23.71 |
| 2014/0161775 A1* | 6/2014 | Weiss | .................. C12N 5/0068 424/93.7 |
| 2014/0242038 A1* | 8/2014 | Hua | ..................... C12N 5/0676 424/93.7 |

FOREIGN PATENT DOCUMENTS

| WO | WO-9841617 A1 * | 9/1998 | .......... C12N 5/0676 |
| WO | 2005/044326 | 5/2005 | |

OTHER PUBLICATIONS de Ferranti et al. Type 1 Diabetes Mellitus and Cardiovascular Disease: A Scientific Statement From the American Heart Association and . Diabetes Care (2014) 37 2843-2863 (Year: 2014).*
Qi et al. The in vivo performance of polyvinyl alcohol macro-encapsulated islets. Biomaterials (2010), 31, 4026-4031 (Year: 2010).*

(Continued)

*Primary Examiner* — Sean C. Barron
(74) *Attorney, Agent, or Firm* — Morgan, Lewis & Bockius LLP

(57) ABSTRACT

The present invention relates to the use of insulin-producing cells encapsulated in silanized hydroxypropyl methylcellulose (Si-HPMC) for the treatment of type 1 diabetes. Methods and kits are also provided for restoring and/or maintaining euglycemia in type 1 diabetic patients and in type 1 prediabetic patients.

9 Claims, 9 Drawing Sheets

(56) References Cited

OTHER PUBLICATIONS

Health Quality Ontario. Pancreas Islet Transplantation for Patients With Type 1 Diabetes Mellitus: A Clinical Evidence Review. Ontario Health Technology Assessment Series; vol. 15: No. 16, pp. 1-84, Sep. 2015 (Year: 2015).*

International Search Report and Written Opinion of the International Searching Authority dated Feb. 13, 2017, which issued during prosecution of International Application No. PCT/EP2016/077193.

Mathieu, et al. "Intramyocardial Delivery of Mesenchymal Stem Cell-Seeded Hydrogel Preserves Cardiac Function and Attenuates Ventricular Remodeling after Myocardial Infarction" PLOS ONE, Dec. 2012, 7(12):e51991.

Risbud, et al. "Islet immunoisolation: experience with biopolymers" J. Biomater. Sci. Polymer Edn., Jan. 2001, 12(11):1243-1252.

Vaithilingam, et al. "Islet Transplantation and Encapsulation: An Update on Recent Developments" The Review of Diabetic Studies, Jan. 2011, 8(1):51-67.

Vinatier, et al. "A silanized hydroxypropyl methylcellulose hydrogel for the three-dimensional culture of chondrocytes" Biomaterials, Nov. 2005, 26(33):6643-6651.

* cited by examiner

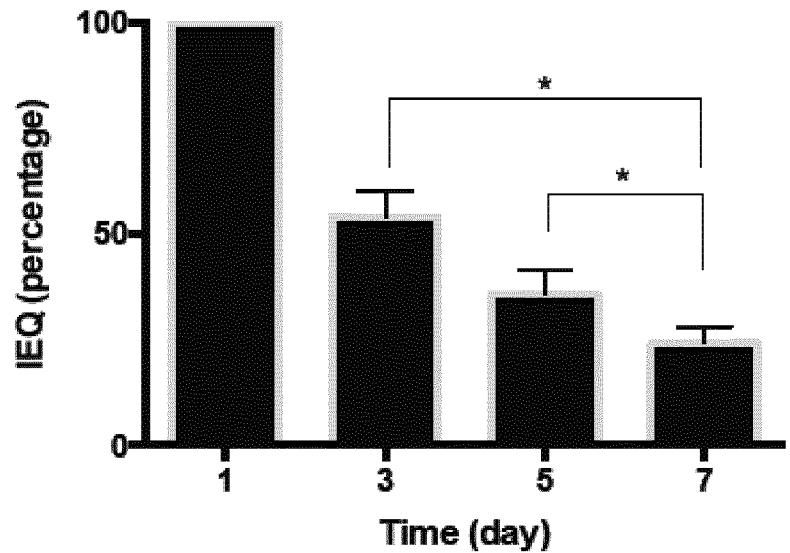
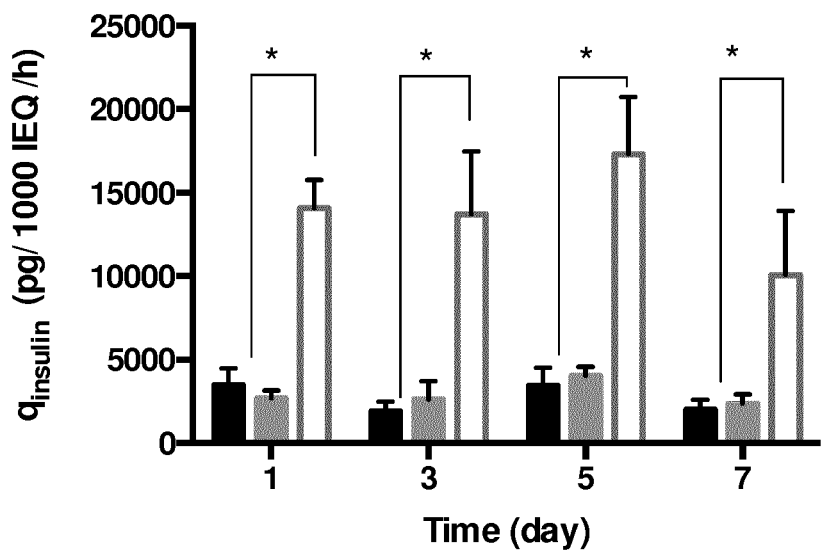
Figure 1(A)-(B)

A
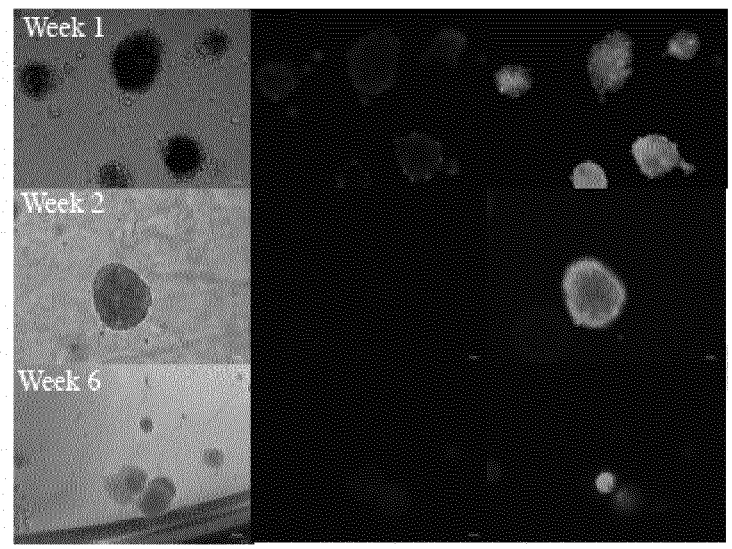
B
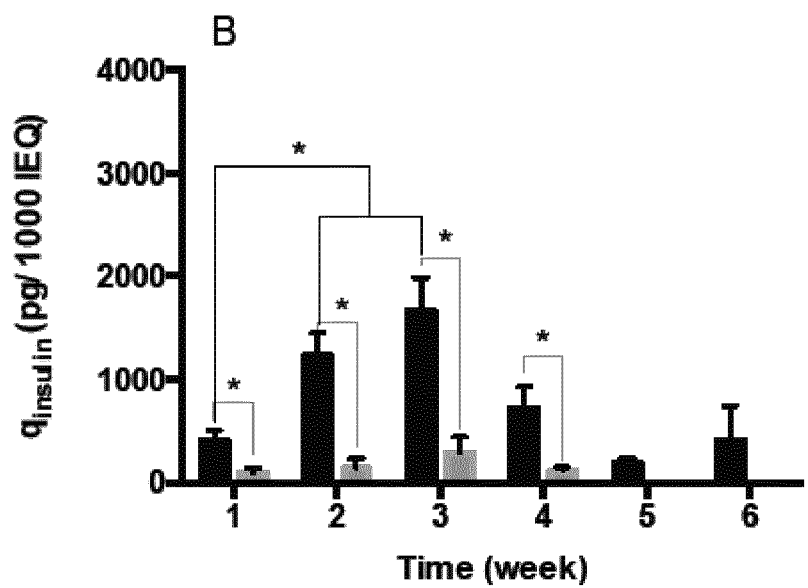
Figure 2(A)-(B)

A
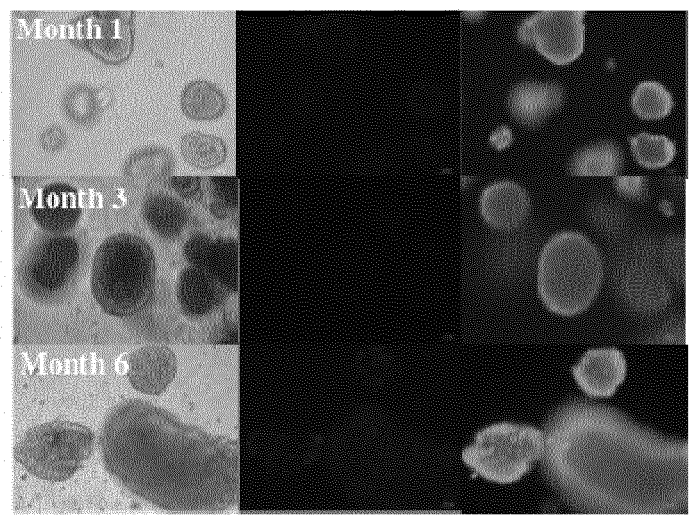
B
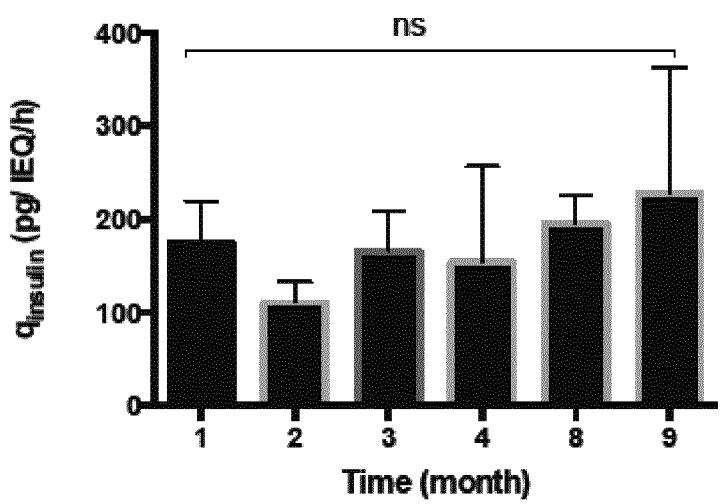
Figure 3(A)-(B)

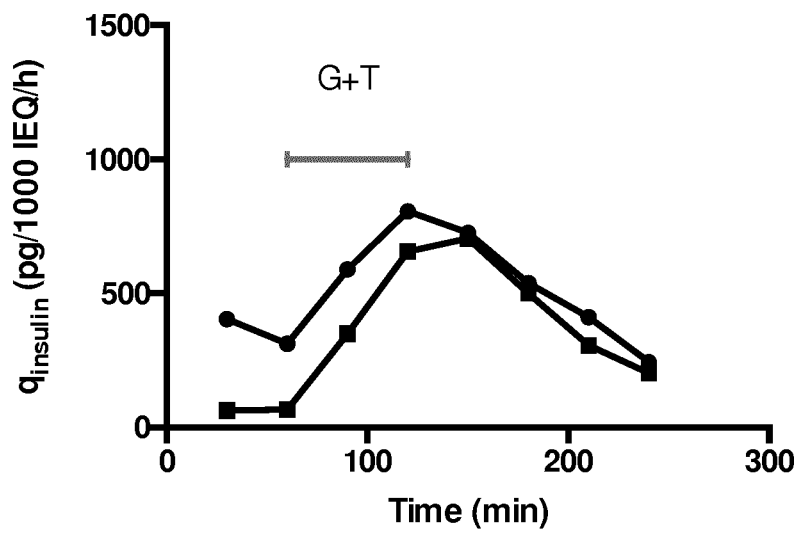
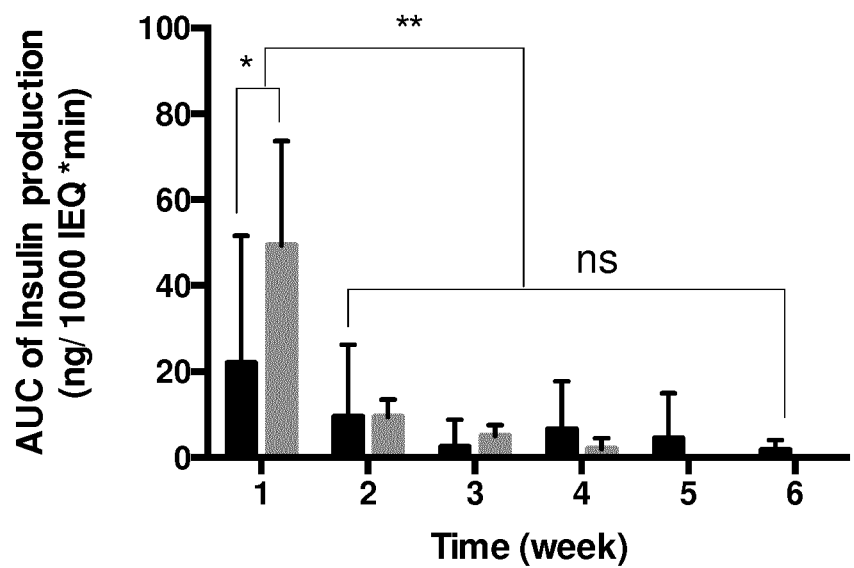
Figure 4(A)-(B)

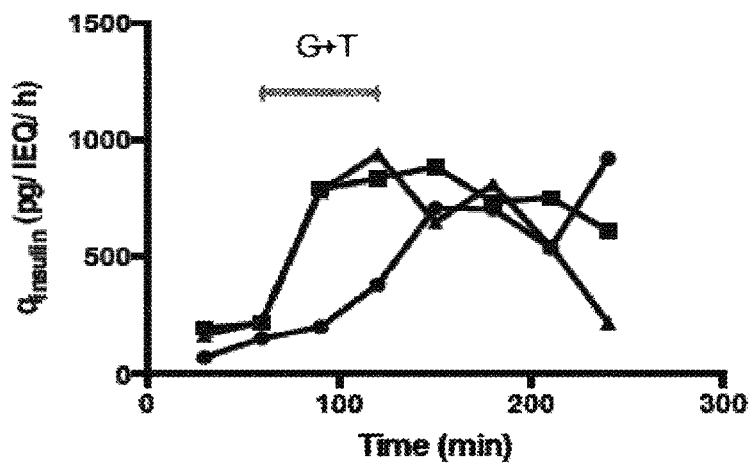
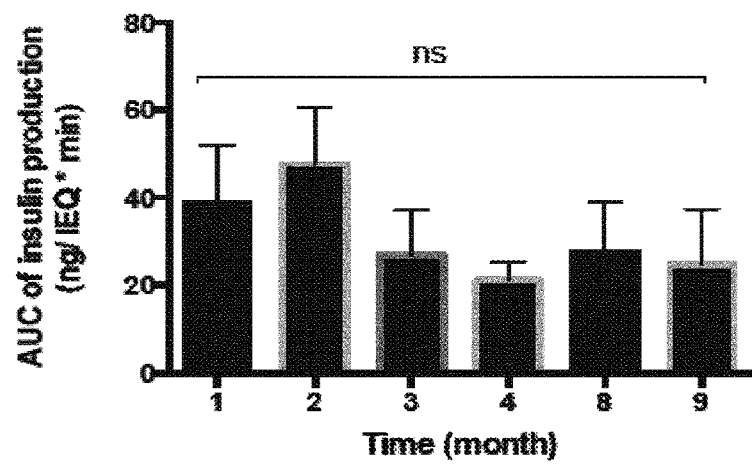
Figure 5(A)-(B)

A
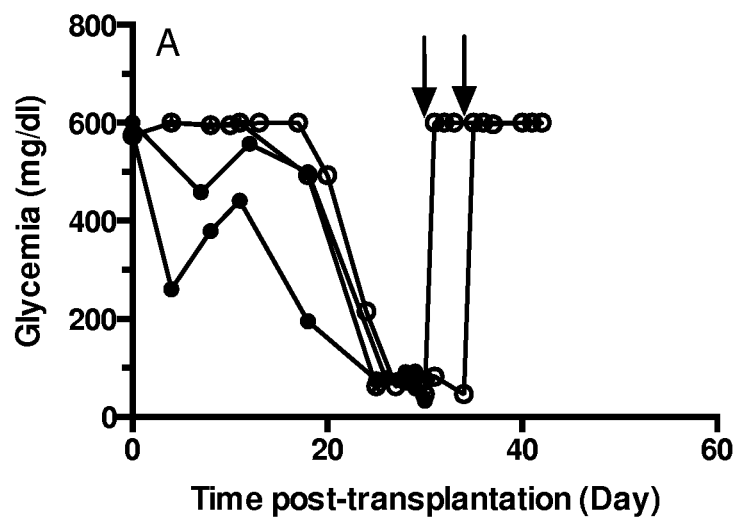
B
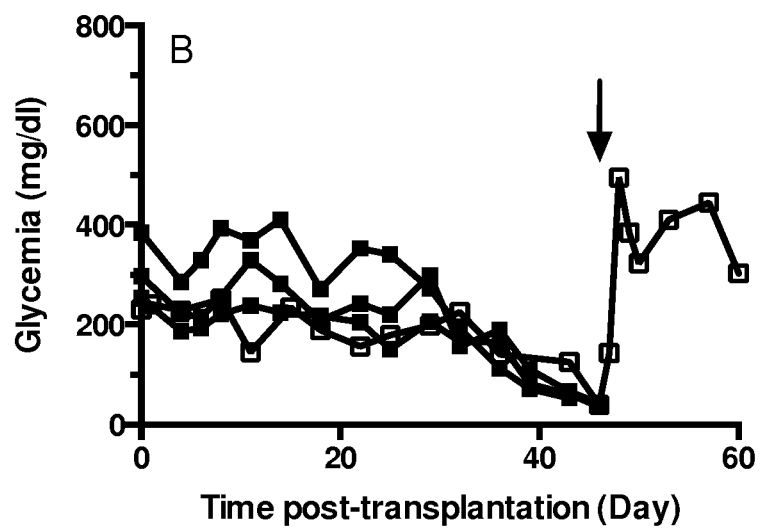
Figure 6(A)-(B)

A
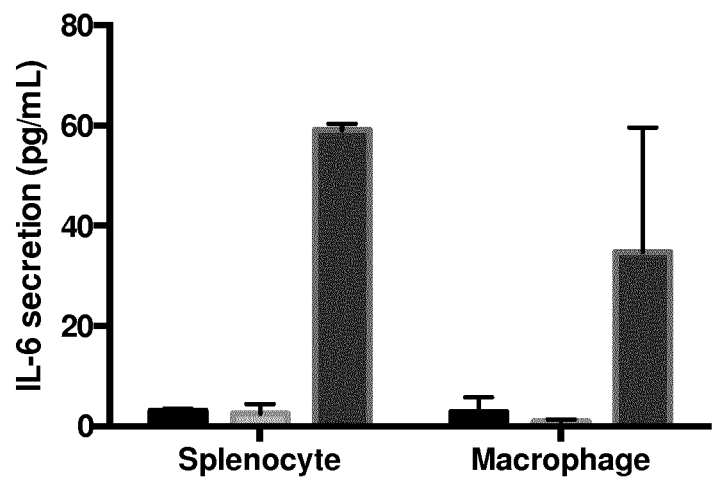
B
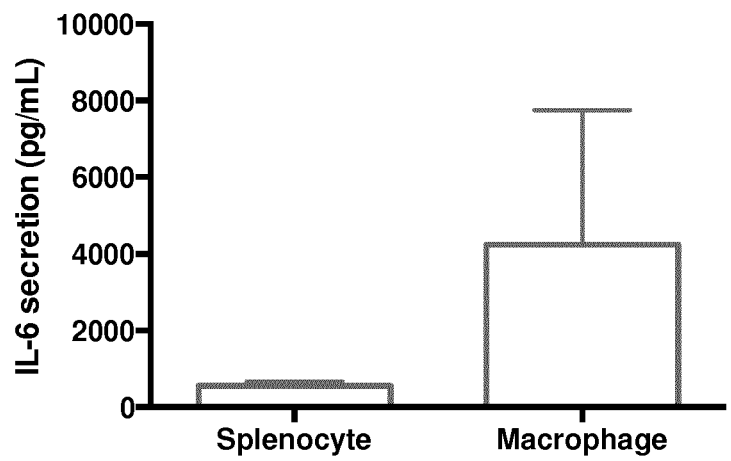
Figure 7(A)-(B)

A
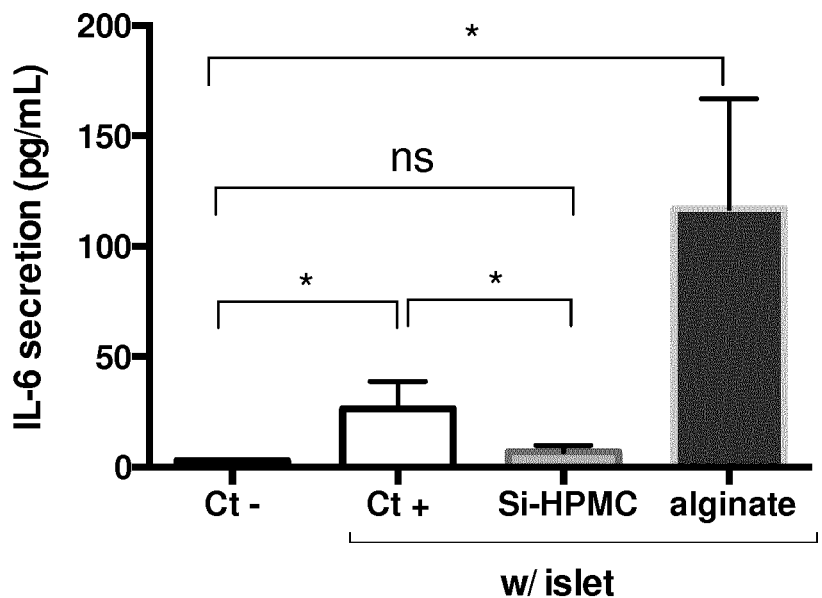
B
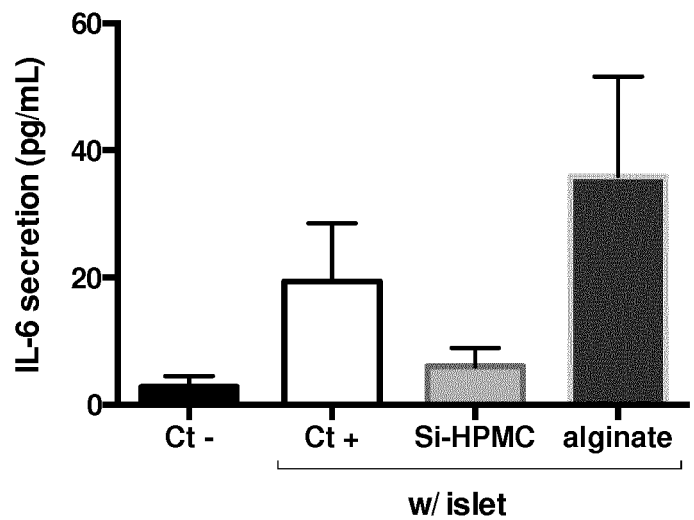
Figure 8(A)-(B)

SI-HPMC-ENCAPSULATED INSULIN-PRODUCING CELLS FOR THE TREATMENT OF TYPE 1 DIABETES

RELATED PATENT APPLICATION APPLICATIONS

The present patent application is filed pursuant to 35 U.S.C § 371 as a U.S. National Phase application of International Patent Application No. PCT/EP2016/077193, which was filed on Nov. 10, 2016, claiming the benefit of priority to European Patent Application No. EP 15 193 861.0 filed on Nov. 10, 2015. The content of each of the aforementioned patent applications is incorporated herein by reference in its entirety.

BACKGROUND OF THE INVENTION

Type 1 diabetes (also known as type 1 diabetes mellitus), which generally develops in children, is a serious chronic disease with an unknown cause. It is characterized by autoimmune destruction of insulin-producing (beta) β-cells in the pancreas. The subsequent lack of insulin leads to increased blood and urine glucose. Globally, type 1 diabetes affects between 15 and 30 million people worldwide (World Health Organization). The incidence of childhood onset diabetes is increasing in many countries (Patterson et al., Diabetes Res. Clin. Pract., 2014, 103: 161-175; Tamayo et al., Diabetes Res. Clin. Pract., 2014, 103: 206-217), with an estimated 80,000 children developing the disease each year. Insulin therapy, which is essential for survival of type 1 diabetes patients, must be continued indefinitely and includes multiple daily injections. In addition to insulin therapy, dietary management is important. Untreated or poorly managed diabetes can cause many complications, including serious long-term complications, which include heart disease, stroke, kidney failure, foot ulcers, damage to the eyes, and coma. In some type 1 diabetics (such as patients with brittle type 1 diabetes—a severe instability of blood glucose levels, which results in disruption of life and often recurrent and/or prolonged hospitalization), complications may also arise from low blood sugar caused by excessive treatment.

One alternative treatment approach to insulin injection is the subcutaneous implantation of insulin pumps. Insulin pump therapy combined with real-time continuous glucose monitoring, known as sensor-augmented pump (SAP) therapy, has been shown to improve metabolic control and to reduce the rate of hypoglycemia in adults with type 1 diabetes compared to multiple daily injections or standard continuous subcutaneous insulin infusion (Deiss et al., Diabetes Care, 2006, 29: 2730-2732; O'Connell et al., Diabetologia, 2009, 52: 1250-1257; Raccah et al., Diabetes Diabetes Care, 2009, 32: 2245-2250; Battelino et al., Diabetologia, 2012, 55: 3155-3162). Despite frequent use in large diabetes centers, continuous glucose monitoring is not commonly employed for pediatric patients (Klonoff et al., J. Clin. Endocrinol. Metab., 2011, 96: 2968-2979; Phillip et al., Pediatr. Diabetes, 2012, 13: 215-228). One reason for this is the lack of infrastructure and personnel qualified to teach patients and their families to use this technology effectively (Tumminia et al., Patient Prefer Adherence, 2015, 9: 1263-1270; Joshi et al., Curr. Diab. Rep., 2015, 15: 81). To lighten the burden of type 1 diabetes for patients and their families, steady progress is being made toward the development of a so-called "artificial pancreas", which may ultimately be a fully automated, closed-loop insulin delivery system combining continuous glucose sensor with insulin infusion pump (or insulin patch pump) using validated mathematical algorithms to drive the continuous insulin infusion (systems developed for example by Medtronic, Abbott, Dexcom, etc. . . . )

Another alternative to exogenous insulin is allotransplantation of pancreatic islets. The Edmonton Protocol has demonstrated the feasibility and success of islet transplantation to restore euglycemia in patients (Shapiro et al., N. Engl. J. Med., 2000, 343: 230-238). However, this procedure, which attempts to replenish the depleted β-cell reserve, is limited by the shortage of human organs of sufficient quality, the need for multiple donors per patient, inconsistent islet yields, the need for immunosuppressive therapy and the resulting deleterious side effects. The minimally invasive subcutaneous transplantation of encapsulated pig or allogenic islets without immunosuppression appears today as a mature therapy (Dufrane et al., Transplantation, 2006, 81: 1345-1353; Elliott et al., Xenotransplantation, 2007, 14: 157-161; Zimmermann et al., Curr. Diab. Rep., 2007, 7: 314-320; Dufrane et al., World J. Gastroenterol., 2012, 18: 6885-6893; Sakata et al., World J. Gastroenterol., 2012, 3: 19-26; O'Sullivan et al., Endocr. Rev., 2011, 32: 827-844; Ramesh et al., Curr. Diabetes Rev., 2013, 9: 294-311; Sharp et al., Adv. Drug Deliv. Rev., 2014, 67-68: 35-73; Zhu et al., Front Surg., 2014, 1: 7; Zhu et al., J. Zhejiang Univ. Sci. B, 2015, 16: 329-343). In encapsulation, cells are encased within a biocompatible matrix, whose primary role is to create, besides an extracellular matrix, a barrier against immune cells and cytotoxic molecules, thus avoiding rejection while still allowing the active diffusion of oxygen, micro- and macro-nutrients, and hormones. However, some last obstacles persist impeding an optimal and durable efficiency this cell therapy. In particular, alginate, which is the standard polymer for islet encapsulation, has several drawbacks: it is difficult to purify and sterilize, it can be immunogenic, it forms hydrogels that are unstable, reversible, that can dissociate and that requires an invasive implantation. Invasive implantations involve an act of surgery which, in addition to common surgical complications, increases the inflammatory response and the risk of rejection.

Thus, there still remains, in the art, an ongoing need for new strategies that can fulfill the promise of establishing islet transplantation as a simple, safe and successful type 1 diabetes therapy.

SUMMARY OF THE INVENTION

The present Inventors have found that silanized hydroxypropyl methylcellulose (Si-HPMC) is a convenient polymer for the encapsulation of insulin-producing cells such as neonate pig islets and murine β-cells. Indeed, Si-HPMC exhibits several advantages: it is biocompatible and easy to sterilize, and its self-reticulation forms covalent and stable bonds. Furthermore, it self-crosslinks (or self-reticulates) at physiological pH and temperature which allows for the non-invasive administration of encapsulated pancreatic islets by injecting Si-HPMC subcutaneously prior to self-crosslinking. The present Inventors have shown that murine encapsulated pancreatic pseudo-islets are able to regulate a streptozotocin-induced diabetes in immunodeficient NOD mice (high dose of streptozotocin) and in immunocompetent C57Bl/6 mice (low dose of streptozotocin). The Si-HPMC hydrogel was found to keep pancreatic murine pseudo-islets and pig islets viable and insulin-secreting for more than 250 and 70 days in vitro, respectively. They also observed that the Si-HPMC hydrogel can prevent the porcine islets-induced secretion of IL-6 by human macrophages and NOD splenocytes in vitro. These results open the way to a realistic and promising cell therapy of type 1 diabetes.

Accordingly, the present invention provides Si-HPMC-encapsulated insulin-producing cells for use in the treatment of type 1 diabetes, in particular for restoring and/or maintaining euglycemia in a type 1 diabetic patient or to a type 1 prediabetic patient. For example, the type 1 diabetic patient may suffer from brittle diabetes.

In certain embodiments, Si-HPMC used in the practice of the present invention has the following simplified formula:

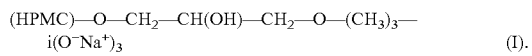

(I).

In certain embodiments, the insulin-producing cells used in the practice of the present invention are isolated allogenic pancreatic islets or isolated xenogenic pancreatic islets.

In certain embodiments, the insulin-producing cells used in the practice of the present invention are isolated cells selected from the group consisting of pancreatic β-cells, pancreatic β-like cells, and any combination thereof. Pancreatic β-cells may be obtained by differentiation of embryonic stem cells, induced pluripotent stem cells, multipotent mesenchymal stromal cells, ductal cells, hepatocytes, or α-cells.

In certain embodiments of the present invention, the insulin-producing cells are micro-encapsulated into Si-HPMC microbeads, Si-HPMC microcapsules, or Si-HPMC microspheres.

In other embodiments, the insulin-producing cells are macro-encapsulated into a Si-HPMC hydrogel.

In certain embodiments of the present invention, the insulin-producing cells are encapsulated in Si-HPMC with at least one therapeutic compound.

In certain embodiments, the treatment of type 1 diabetes involves one of: subcutaneous injection of the Si-HPMC-encapsulated insulin-producing cells, intramuscular injection of the Si-HPMC-encapsulated insulin-producing cells, implantation of the Si-HPMC-encapsulated insulin-producing cells in the peritoneal cavity, in the mesentery, in the omemtum, or in the renal capsule.

In certain embodiments, the treatment of type 1 diabetes further comprises administration of an insulin-therapy to the patient.

In another aspect, the present invention provides a kit for use in the treatment of type 1 diabetes, in particular for restoring and/or maintaining euglycemia in a type 1 diabetic patient or to a type 1 prediabetic patient, said kit comprising Si-HPMC-encapsulated insulin-producing cells as described herein.

The present invention also provides a kit for use in the treatment of type 1 diabetes, in particular for restoring and/or maintaining euglycemia in a type 1 diabetic patient or a type 1 prediabetic patient, said kit comprising: Si-HPMC; insulin-producing cells; and instructions to encapsulate the insulin-producing cells in Si-HPMC, as described herein.

In a related aspect, the present invention provides a method of treatment of type 1 diabetes, in particular for restoring and/or maintaining euglycemia in a type 1 diabetic patient or to a type 1 prediabetic patient, the method comprising a step of administering to said patient a therapeutically effective amount of Si-HPMC encapsulated insulin-producing cells as described herein.

These and other objects, advantages and features of the present invention will become apparent to those of ordinary skill in the art having read the following detailed description of the preferred embodiments.

DEFINITIONS

Throughout the description, several terms are employed that are defined in the following paragraphs.

As used herein, the term "biomaterials" refers to materials that are intended to come into contact with biological fluids or tissues (such as by implantation or transplantation into a subject). It is desirable that biomaterials induce minimal reactions with the physiological environment. Biomaterials are considered "biocompatible" if, after being placed in the physiological environment, there is minimal inflammatory reaction, no evidence of anaphylactic reaction, and minimal cellular growth on the biomaterial surface. Upon implantation/transplantation in a host mammal, a biocompatible material such as a hydrogel does not elicit a host response sufficient to detrimentally affect the function of the hydrogel; such host responses include formation of fibrotic structures on or around the hydrogel, immunological rejection of the hydrogel, or release of toxic or pyrogenic compounds from the hydrogel into the surrounding host tissue and/or fluid.

As used herein, the term "hydrogel" refers to a three-dimensional network of cross-linked hydrophilic polymers. The network is in the form of a gel substantially composed of water, preferably, but not limited to, gels being greater than 90% water. Cross-linked hydrogels can also be considered solids because they do not flow or deform without appreciable applied shear stress.

The term "encapsulation", as used herein, has its art understood meaning, and refers to the containment, immobilization and/or entrapment of a cell or cells within a three-dimensional structure (e.g., a capsule, a hydrogel, etc. . . . ) delineated by a physical barrier (i.e., a barrier that reduces or controls the permeability of said structure). In the practice of the present invention, encapsulation may be performed by microencapsulation or by macroencapsulation. As known in the art, in microencapsulation methods, a smaller cell mass is individually entrapped in its own spherical polymer capsule (with a diameter of about 0.3 mm to about 2 mm, for example) or polymer layer. In macro-encapsulation methods, cells are enclosed between two or more selectively permeable flat sheet membranes or within the lumen of a semipermeable hollow fiber or yet within a hydrogel. Macroencapsulation entails the entrapment of a large number of cells and allows cells to be implanted and removed easily. In contrast, microencapsulated cells are irretrievable after transplantation. One skilled in the art knows what cell microencapsulation and cell macroencapsulation mean (Uludag et al., Advanced Drug Delivery Reviews, 2000, 42: 29-64). In particular, one skilled in the art knows that cell microencapsulation devices include, but are not limited to, spherical capsules with a diameter of about 0.3 mm to about 2 mm (traditionally referred to as microcapsules), microbeads, and conformal coating where the surface of a cell mass is surrounded with a membrane. One skilled in the art knows that, compared to microcapsules, macrocapsules are much larger devices and typically possess a planar or cylindrical geometry and a smaller surface-to-volume ratio. Thus, one skilled in the art knows that macroencapsulation devices include, but are not limited to, flat-sheet membranes (which consist of two planar membranes that are attached to either side of a spacer element to create an internal compartment or encapsulation chamber) and hollow fiber membranes (which utilize a preformed hollow fiber membrane in which cells are infused into the lumen and the ends are subsequently sealed).

As used herein, the terms "cells" refers to cells in various forms, including but not limited to cells retained in tissues, cell clusters (such as pancreatic islets or portions thereof), and individually isolated cells.

The term "isolated", when used herein to refer to cells, means cells which, by virtue of their origin or manipulation, are separated from at least some of the components with which they are naturally associated or with which they are associated when initially obtained or prepared.

As used herein, the term "subject" refers to a human or another mammal (e.g., primate, dog, cat, goat, horse, pig, mouse, rat, rabbit, and the like) that can develop type 1 diabetes, but may or may not have the disease. Non-human subjects may be transgenic or otherwise modified animals. In many embodiments of the present invention, the subject is a human being. In such embodiments, the subject is often referred to as an "individual" or a "patient". The terms "subject", "individual" and "patient" do not denote a particular age, and thus encompass newborns, children, teenagers, and adults. The term "patient" more specifically refers to an individual suffering from a disease (e.g., type 1 diabetes).

The term "treatment" is used herein to characterize a method or process that is aimed at (1) delaying or preventing the onset of a disease or condition (here type 1 diabetes); (2) slowing down or stopping the progression, aggravation, or deterioration of the symptoms of the disease or condition; (3) bringing about amelioration of the symptoms of the disease or condition; or (4) curing the disease or condition. A treatment may be administered after initiation of the disease or condition, for a therapeutic action. Alternatively, a treatment may be administered prior to the onset of the disease or condition, for a prophylactic or preventive action. In this case, the term "prevention" is used.

As used herein, the term "therapeutically effective amount" refers to any amount of a therapeutic agent, or composition thereof, that is sufficient to fulfil its intended purpose(s), e.g., a desired biological or medicinal response in a cell, tissue, system or subject. For example, in certain embodiments of the present invention, the purpose(s) may be: to restore and/or maintain euglycemia in type 1 diabetic patients.

The terms "euglycemia" and "normoglycemia" are used herein interchangeably. They have their art understood meaning and refer to the condition of having a normal (i.e., healthy) blood glucose concentration. The term "hypoglycemia" refers to a blood glucose condition that is below than normal, and the term "hyperglycemia" refers to a blood glucose condition that is higher than normal.

The terms "approximately" and "about", as used herein in reference to a number, generally include numbers that fall within a range of 10% in either direction of the number (greater than or less than the number) unless otherwise stated or otherwise evident from the context (except where such number would exceed 100% of a possible value).

DETAILED DESCRIPTION OF CERTAIN PREFERRED EMBODIMENTS

As mentioned above, Si-HPMC is described herein as an advantageous polymer for the encapsulation of insulin-producing cells and the invention relates to the use of Si-HPMC-encapsulated insulin-producing cells in the management of type 1 diabetes, in particular for restoring and/or maintaining euglycemia in type 1 diabetic patients.

I—Si-HPMC for Encapsulation of Insulin-producing Cells

A. Silanized Hydroxylpropylmethylcellulose (Si-HPMC)

As used herein, the term "Si-HPMC" refers to a silanized (i.e., silytated) hydroxypropylmethylcellulose (HPMC), and more particularly to the silanized HPMC that was developed by the team of Professor Guicheux and Professor Weiss (Laboratoire d'Ingénierie Ostéo-Articulaire et Dentaire, LIOAD, Nantes, France).

This polymer (Si-HPMC) has already found several applications a biocompatible material. Indeed, it has been used for the three-dimensional culture of chondrocytes (Vinatier et al., Biomaterials, 2005, 26: 6643-6651); of osteogenic cells (Trojani et al., Biomaterials, 2005, 26: 5509-5517); and of human adipose-derived mesenchymal stem cells (Merceron et al., Cell Transplant, 2011, 20: 1575-1588; Porton et al., PLoS One, 2013, 8(4): e62368). It was found to be a suitable scaffold for human nasal chondrocytes-based cartilage engineering (Vinatier et al., J. Biomed. Mater Res. A, 2007, 80: 66-74) and a suitable injectable hydrogel for the transfer of autologous nasal chondrocytes in articular cartilage defects (Vinatier et al., Biotechnol. Bioeng., 2009, 102: 1259-1267). It has been used as a composite in combination with calcium phosphate loaded with undifferentiated bone marrow stromal cells for ectopic bone formation (Trojani et al., Biomaterials, 2006, 27: 3256-3264). Si-HPMC was also incorporated with glycosaminoglycan-like marine exopolysaccharides for bone and cartilage tissue engineering (Rederstorff et al., Acta Biomater., 2011, 7(5): 2119-2130). An intramyocardial delivery of mesenchymal stem cell-seeded Si-HPMC hydrogel was shown to preserve cardiac function and attenuate ventricular remodeling after myocardial infarction (Mathieu et al., PLoS One, 2012, 7(12): e51991).

Si-HPMC, developed by the team of Professor Guicheux and Professor Weiss and used in the practice of the present invention, is an injectable and self-setting (or self-hardening) polymer consisting of hydroxypropylmethylcellulose grafted with silane groups which, upon pH decrease, allow the formation of covalent bonds between the HPMC chains (see below). Si-HPMC has been described, for example, in WO 2005/044326, U.S. Pat. Appln. No. U.S. 2007/021289, U.S. Pat. Appln. No. 2010/080836 and U.S. Pat. Appln. No. US 2014/016775). Its rheological and gelling properties have been studied (Fatimi et al., Biomaterials, 2008, 29(5): 533-543; Fatimi et al., Acta Biomateriala, 2009, 5(9): 3423-3432, Mathieu et al., PLoS One, 2012, 7(12): e51991).

More specifically, Si-HPMC used in the practice of the present invention consists of a polymer of simplified formula: (HPMC)—O—X—Si(OZ)$_3$, which may be obtained by the reaction of HPMC with a compound of formula X—Si(OZ)$_3$, wherein X represents a halogen atom or a hydrocarbon group, in particular a $C_2$-$C_{20}$ hydrocarbon group, comprising an epoxy function, and wherein Z is selected from the group consisting of a hydrogen atom, an alkali metal and an alkyl group, in particular a $C_1$-$O_5$ alkyl group.

In certain preferred embodiments, the compound of formula X—Si(OZ)$_3$ is (3-glycidoxypropyl)trimethoxysilane, which has the following formula:

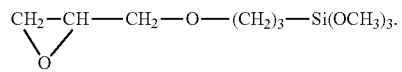

In a basic medium, the 3-glycidoxypropyltrimethoxysilane is grafted onto the HPMC by opening of the epoxide, and the methoxysilane groups are hydrolyzed to produce Si-HPMC of simplified formula (I):

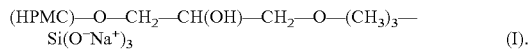

(HPMC)—O—CH$_2$—CH(OH)—CH$_2$—O—(CH$_2$)$_3$—Si(O$^-$Na$^+$)$_3$     (I).

In the practice of the present invention, Si-HPMC may be prepared using any suitable method. However, in certain preferred embodiments, Si-HPMC has the simplified formula (I) and is prepared as previously described (Fatimi et al., Biomaterials, 2008, 29: 533-543; Vinatier et al., Biomaterials, 2005, 26: 6643-6651). Briefly, starting HPMC is Methocel® EA4 Premium (from the Dow Chemical Company, M$_w$=290,000 g/mol, wherein the methoxyl content is 29% and the hydroxypropyl content is 9.7%, corresponding to an average degree of substitution (DS) of 1.9 and to a an average degree of molar substitution (MS) of 0.23). Silane grafting on HPMC involves a Williamson reaction between a hydroxyl function of HPMC and the epoxide group of the silane. As described by Vinatier et al., (Biomaterials, 2005, 26: 6643-6651), Si-HPMC is synthesized by grafting 14.24% of 3-glycidoxypropyltrimethoxysilane onto HPMC (Methocel® EA4 Premium) in heterogeneous medium.

Before it is used for a treatment according to the present invention, Si-HPMC may be stored in the form of a powder. Alternatively, Si-HPMC, which is stable in aqueous solution at a pH greater than or equal to approximately 12.4, may be stored in an alkaline sodium hydroxide solution (pH≥12.4).

B. Insulin-Producing Cells

As used herein, the term "insulin producing cell" refers to any cell that is capable of producing insulin.

In certain embodiments, the insulin-producing cells to be used in the practice of the present invention are isolated pancreatic islet cells. Approximately one percent of the volume of the human pancreas is made up of islets of Langerhans (or "islets"), which are scattered throughout the exocrine pancreas. Each islet comprises insulin producing β-cells as well as glucagon-containing α-cells, somatostatin secreting delta cells, and pancreatic polypeptide-containing cells (PP-cells). The majority of islet cells are insulin-producing β-cells. The expression of specific surface antigens is used to determine whether a cell is a pancreatic β-cell. For instance, pancreatic β-cells express the glucose transporter, Glut-1 and/or Glut-2. Alternatively, the expression of specific transcription factors is used to determine whether a cell is a pancreatic β-cell. For instance, β-cells highly express the transcription factors Pdx1, Nkx6.1, MafA and PaxA. Lastly, electron microscopy observation can be used to ascertain atypical β-cell ultrastructure.

Pancreatic islet cells for use in the practice of the present invention may be allogenic pancreatic islet cells or xenogenic pancreatic islet cells. As used herein, the terms "allogenic" and "xenogenic" have their art-understood meanings. When used in reference to cells, the term "allogenic" refers to cells that were not obtained from the subject to which they are to be delivered, but from a donor of the same species as the patient to be treated. When used in reference to cells, the term "xenogenic" refers to cells that were obtained from a donor from a species that is different from the species of the patient to which the cells are to be delivered.

As known in the art, pancreatic islets obtained from pigs have emerged as an alternative to human islets due to their great availability, physiological similarities to human islets, including the time-tested use of porcine-insulin in diabetic patients and the ability to genetically modify the donor source. Many studies have successfully demonstrated the use of porcine islets in achieving reversal of diabetes in non-human primates (reviewed by Van der Windt et al., Diabetes, 2012, 61: 3046-3055). Pig islet transplantation in humans has been reported by several groups (Groth et al., Lancet, 1994, 344: 1402-1404; Elliott et al., Xenotransplantation, 2007, 14: 157-161; Valdes-Gonzales et al., Clin. Exp. Immunol. 2010, 162: 537-542; Elliot, Curr. Opin. Organ Transplant, 2011, 16: 195-200; Elliot et al., Xenotransplantation, 2013, 20: 49) although the outcomes have to date largely been unsuccessful. Various techniques to improve graft survival are being tested, for example microencapsulation (Dufrane et al., Transplantation, 2010, 90: 1054-1062) and co-culture with Sertoli cells (Isaac et al., Transplant. Proc., 2005, 37: 487-488). Pigs with various genetic modifications have been produced to resist immune-mediated rejection of islet grafts (Van der Windt et al., Diabetes, 2012, 61: 3046-3055; Phelps et al., Science, 2003, 299: 411-414; Yares et al., Xenotransplantation, 2007, 14: 428; Van der Windt et al., Am. J. Transplant., 2009, 9: 2716-2726; Thompson et al., Am. J. Transplant, 2011, 11: 2593-2602), and several immunosuppressive regimens have been explored to reduce islet graft rejection (Van der Windt et al., Am. J. Transplant., 2009, 9: 2716-2726; Hering et al., Nature Med., 2006, 12: 301-303; Cardona et al., Nature Med., 2006, 12: 304-306; Cardona et al., Am. J. Transplant., 2007, 7: 2260-2268; Thompson et al., Am. J. Transplant, 2011, 11: 947-957). Thus, research in the field of islet xenotransplantation has demonstrated that it may translate into routine clinical care.

Pancreatic islets for use in the practice of the present invention may be isolated using any suitable method. Methods of isolating viable pancreatic islet cells are known in the art (see for example, Field et al., Transplantation, 1996, 61: 1554; Linetsky et al., Diabetes, 1997, 46: 1120). For example, porcine islets or islet cells can be harvested from adult pig pancreas, neonate pig pancreas or fetal pig pancreas according to methods known in the art (see, for example, Swanson et al., Human Immunology, 2011, 62: 739-749; Casu et al., Diabetologia, 2008, 51: 120-129; Cantorovich et al., Xenotransplantation, 2002, 9: 25-35; Groth et al., J. Mol. Med., 1999, 77: 153-154; Korbutt et al., J. Clin. Invest., 1996, 97: 2119-2129). For example, human islets can be isolated from human cadaver pancreas according to methods known in the art (see, for example, Shapiro et al., N. Engl. J. Med., 2000, 343: 230-238; Lablanche et al., Diabetes Care, 2015, 38: 1714-1722).

Fresh pancreatic tissue can be divided by mincing, teasing, comminution and/or enzymatic digestion (for example collagenase digestion). The islets are then isolated from contaminating cells and materials by washing, filtering, centrifuging and/or picking procedures. Methods and apparatus for isolating and purifying islet cells are described in U.S. Pat. Nos. 5,447,863, 5,322,790, 5,273,904, and 4,868,121. The isolated pancreatic cells may optionally be cultured prior to encapsulation, using any suitable method of culturing islet cells as is known in the art (see, for example, U.S. Pat. No. 5,821,121). Isolated cells may be cultured in a medium under conditions that helps to eliminate antigenic components.

Prior to encapsulation, isolated pancreatic islets may be cultured. The islets may be cultured according to known cell culture techniques for a period of at least 3 hours, or more preferably for a period of 12-36 hours, such as for example for a period of 18-24 hours, in a culture medium containing agents to improve glucose-stimulated insulin secretion, such as: an antioxidant (e.g., lutathione or glutathione analogs, glutathione monoester, and N-acetylcysteine and/or superoxide dismutase, catalase, vitamin E, Trolox, lipoic acid, lazaroids, butylated hydroxyanisole (BHA), vitamin K, and the like), an anti-cytokine (e.g., dimethylthiourea, citiolone, pravastatin sodium, L-N$^G$-monomethylarginin, lactoferrin, 4-methylprednisolone, and the like), an anti-endotoxin (e.g., L-N$^G$-monomethylarginine, lactoferrin, N-acetylcysteine, adenosine receptor antagonists such as bamiphylline (theophylline) and anti-lipopolysaccharide compounds such as echinomycine, and the like), and an antibiotic (e.g., penicillins, tetracyclines, cephalosporins, macrolides, β-lactams and aminoglycosides; examples of such suitable antibiotics include streptomycin and amphotericin B).

The viability and functionality of isolated pancreatic β-cells may be assessed prior to encapsulation. For example, porcine islet cells can be assessed for islet function by a static incubation test (see, for example, Cantarovich et al., Xenotransplantation, 2002, 9: 23-35).

As used herein, the term "insulin producing cell" also refers to a cell differentiated from a pancreatic progenitor, or precursor thereof, which secretes insulin. Insulin-producing cells includes pancreatic β-cells and pancreatic β-like cells (i.e., insulin-positive, endocrine cells) that synthesize (i.e., transcribe the insulin gene, translate the proinsulin mRNA, and modify the proinsulin mRNA into the insulin protein), express (i.e., manifest the phenotypic trait carried by the insulin gene), or secrete (i.e., release insulin into the extracellular space) insulin in a constitutive or inducible manner. "Pancreatic β-like cells" are defined as cells produced by differentiation from a pancreatic progenitor, or precursor thereof, and which express at least 15% of the amount of insulin expression by an endogenous functioning pancreatic β-cell, or at least about 20%, at least about 30%, at least about 40%, at least about 50%, at least about 60%, at least about 70%, at least about 80%, at least about 90%, at least about 100% or greater than 100%, such as at least about 1.5 fold, or at least about 2-fold, at least about 2.5-fold, at least about 3-fold, at least about 4-fold, at least about 5-fold or more than about 5-fold the amount of the insulin secreted by an endogenous pancreatic β-cell, or alternatively exhibits at least one, or at least two characteristics of an endogenous pancreatic β-cell, for example, but not limited to, secretion of insulin in response to glucose, and expression of β-cell markers, such as for example, c-peptide, Pdx1 and Glut-1 and/or Glut-2.

Thus, in certain embodiments, the insulin-producing cells to be used in the practice of the present invention are pancreatic β-cells or pancreatic β-like-cells that are derived from embryonic stem cells, induced pluripotent stem cells, or multipotent mesenchymal stromal cells.

Embryonic stem cells (ESCs) have several advantages over other potential sources because they are now readily available, are highly expandable, and can be differentiated to β-cells (Mfopou et al., Diabetes, 2010, 59: 2094-2101). Many studies have demonstrated the derivation of Pdx1+ or endocrine cells from ESCs, and some groups have generated insulin- or C-peptide-secreting cells (Soria et al., Diabetes, 2000, 49: 157-162; Mao et al., Biomaterials, 2009, 30: 1706-1714; Zhang et al., Cell Res., 2009, 19: 429-438).

Induced pluripotent stem cells (iPSCs) are another important source of stem cells that are being studied for use in islet transplantation. They have the unique property of allowing the generation of autologous cells that might be useful for therapy (Takahashi, Cell. 2007, 131: 861-872). The β-cell differentiation potential of iPSCs has been shown in vitro with demonstration of partial glucose-responsive C-peptide release (Zhang et al., Cell Res., 2009, 19: 429-438; Tateishi et al., J Biol Chem., 2008, 283: 31601-31607; Maehr et al., Proc. Natl. Acad. Sci. USA, 2009, 106: 15768-15773). Moreover, recent studies have highlighted the potential of mouse (Alipio et al., Proc. Natl. Acad. Sci. USA, 2010, 107: 13426-13431) and rhesus monkey (Zhu et al., Diabetologia, 2011, 54: 2325-2336) iPSCs to reverse hyperglycemia after in vitro differentiation and transplantation in diabetic mouse models. Reversal of diabetes was also observed in mice with insulin-producing cells derived in vitro from human pluripotent stem cells (Rezania et al., Nature Biotechnology, 2014, 32: 1121-1133).

Multipotent mesenchymal stromal cells (MSCs) are easily isolated from many tissue sources, are highly expandable in vitro, are resistant to cryopreservation, and have the potential to differentiate into many different lineages. Reversal of diabetes has been reported with human MSCs that differentiate into insulin$^+$ cells after transplantation into STZ-diabetic rats without immunosuppression (Chao et al., PloS One, 2008, 3: e1451). Different MSCs sources such as cord blood, adipose tissue, and bone marrow have been used to generate insulin-producing cells (Chao et al., PloS One, 2008, 3: e1451; Kajiyama et al., Int. J. Dev. Biol., 2010, 54: 699-705; Xie et al., Differentiation, 2009, 77: 483-491; Allahverdi et al., Cell J., 2015, 17: 231-242).

In addition to all the aforementioned cell types, pancreatic epithelial cells such as ductal cells (Seaberg et al., Nature Biotechnol., 2004, 22: 1115-1124; Bonner-Weir et al., Proc. Natl. Acad. Sci. USA, 2000, 97: 7999-8004; Gao et al., Diabetes, 2003, 52: 2007-2015, Hao et al., Nature Med, 2006, 12: 310-316), hepatocytes (Ferber et al., Nature Med., 2000, 6: 568-572; Sapir et al., Proc. Natl. Acad. Sci. USA, 2005, 102: 7964-7969; Kaneto et al., Diabetes, 2005, 54: 1009-1022), and even α-cells (Collombat et al., Cell, 2009, 138: 449-462; Thorel et al., Nature, 2010, 464: 1149-1154; Gianani et al., Semin Immunopathol., 2011, 33: 23-27) have been demonstrated to be able to differentiate into pancreatic β-cells under appropriate conditions (Lysy et al., Stem Cells Transl. Med., 2012, 1: 150-159).

C. Preparation of Si-HPMC-Encapsulated Insulin-Producing Cells

Encapsulation of insulin-producing cells in Si-HPMC may be carried out using any suitable macroencapsulation or microencapsulation technique known in the art (reviewed by Uludag et al., Drug Delivery Reviews, 2000, 42: 29-64). Encapsulation is aimed at surrounding an insulin-producing cell or group of insulin-producing cells with a material barrier in order to protect the transplanted encapsulated cells from host immune rejection. The method of preparation of the Si-HPMC-encapsulated insulin-producing cells is not a limiting factor, as long as it allows the cells to remain viable and to function properly when introduced into a patient.

Encapsulation using Si-HPMC takes advantage of the gelling properties of Si—HPMC as a function of pH.

As mentioned above, Si-HPMC is a self-hardening (or self-setting) polymer consisting of hydroxyprogylmethylcellulose grafted with silane groups which, upon pH decrease, allow the formation of covalent bonds between the HPMC chains (see below). While, Si-HPMC is stable in aqueous solution at pH greater than or equal to 12.4, acidification of the solution causes a gradual increase in viscosity and the formation of a hydrogel. The gelation pH is between 7 and 12, depending on the desired rate of cross-linking. This physical phenomenon accompanies the cross-linking of Si-HPMC through (i) transformation of the silanolate groups (—Si(O$^-$Na$^+$)$_3$) into silanol groups (—Si (OH)$_3$) and then formation of a three-dimensional network by (ii) condensation of a first silanol group on one Si-HPMC molecule with a second silanol group on a different Si- HPMC molecule and/or condensation of a silanol group on one Si-HPMC molecule with a hydroxyl group of the HPMC chain on a different Si-HPMC molecule. Conditions (in particular pH and temperature) may be selected to control the rate of crosslinking of Si-HPMC (Bourges et al., Adv. Colloid Interface Sci. 2002, 99: 215-228).

In general, micro- and macro-encapsulation of insulin-producing cells in Si—HPMC will comprise a step wherein the cells are incorporated into a solution of Si—HPMC under the form of a viscous liquid. Such a Si-HPMC viscous liquid may be obtained as previously described (Fatimi et al., Biomaterials, 2008, 29: 533-543; Vinatier et al., Biomaterials, 2005, 26: 6643-6651). Briefly, Si-HPMC powder (3% w/v) may be solubilized in 0.2 M NaOH (3%) under constant stirring for 48 hours at room temperature. The solution may then be sterilized, for example, by steam (at 121° C. for 20 minutes). Finally, to allow the formation of a reticulated hydrogel, the solution is mixed with 0.5 volume of 0.26 M HEPES buffer. The final product is a viscous liquid at pH 7.4, which allows cell incorporation. As will be recognized by one skilled in the art, variations of this method can be easily designed.

For example, a Si-HPMC viscous liquid may be obtained as previously described or as described in the Examples below. Briefly, Si-HPMC is dissolved in 0.2 M NaOH aqueous solution (30.9 mg/mL, pH>12.5), then 2 dialyses with the molecular weight cut off of 6-8 kDa are performed in 0.09 M $NaOH_{aq}$, in order to eliminate any non-grafted 3-glycidoxypropyltrimethoxysilane from the Si-HPMC powder. The hydrogel precursor solution is then obtained by mixing one volume of the Si-HPMC basic solution contained in one luer-lock syringe with 0.5 volume of an acidic buffer solution in another luer-lock syringe, by interconnecting both syringes. The acidic buffer solution at pH 3.2 may be prepared by mixing 6.2 g of 4-(2-hydroxyethyl)-1-piperazineethanesulfonic acid (HEPES≥99.5%), 1.8 g of NaCl (≥99%) and 60 mL of 0.1 M HCl aqueous solution (HCl 37 wt %). The volume is adjusted to 100 mL with deionized water to reach a final pH of 7.4. This mixture is then injectable for 30-40 minutes until the gel point is reached. Using the same process, a suspension of islets or cell islets (i) may be added, before crosslinking, in a third luer-lock syringe and connected with the final viscous solution of Si-HPMC, or (ii) may be introduced, before crosslinking, in the final viscous solution of Si-HPMC, as described herein.

In certain embodiments, insulin-producing cells are microencapsulated in Si—HPMC. Microencapsulation allows single or groups of insulin-producing cells (e.g., islets) to be immuno-isolated from the host system via spherical droplets/beads or multilayering systems. This form of encapsulation has been the most intensely studied over the past three decades due to ease of production, mechanical stability, large surface-to-volume ration, and optimal diffusion capability. The size of microspheres in early studies ranged from 600 to 800 μm; however, recent fabrication techniques have allowed 350 to 500 μm microspheres to be produced. However, microspheres, microcapsules or microbeads may be smaller than 350 μm and larger than 800 μm.

Microencapsulation of insulin-producing cells in Si-HPMC generally comprise three steps: incorporation of the insulin-producing cells within a viscous solution of Si—HPMC (under the form of a pre-gel); dispersion of the cells into small droplets, thereby producing microcapsules; and stabilization of the droplets by crosslinking (or self-reticulation) of Si-HPMC using a biological buffer of an appropriate pH. Examples of suitable biological buffers include phosphate buffers (PBS, phosphate buffered saline), HEPES and TRIS buffer. Any biological medium known to a person skilled in the art, for example DMEM medium or alpha-MEM medium (alpha minimum essential medium), may also be used. The Si-HPMC microcapsules containing insulin-producing cells may then be stored (at physiological pH (7.4) and temperature (37° C.)) for a period as short as a few hours, and as long as several days under culture conditions in an incubator at 37° C., 5% $CO_2$ with regular culture medium renewal.

Cells suspended in a gellable medium (i.e., Si-HPMC) may be formed into droplets using any suitable method known in the art, including but not limited to emulsification (e.g., U.S. Pat. No. 4,352,883), extrusion from a needle (e.g., U.S. Pat. No. 4,407,957; Nigam et al., Biotechnology Techniques, 1988, 2: 271-276), use of a spray noodle (Plunkett et al., Laboratory Investigation, 1990, 62: 510-517) or use of a needle and pulsed electrical electrostatic voltage (e.g., U.S. Pat. Nos. 4,789,550 and 5,656,468)

In certain embodiments, insulin-producing cells are macroencapsulated in Si—HPMC. In contrast to microencapsulation, macroencapsulation encloses a larger number of insulin-producing cells in a larger device or hydrogel that can be handled macroscopically. Macroencapsulated islets are easy to retrieve if adverse events (such as infection) occur, and easy to replace if function decays with time.

In certain embodiments, the hydrogel containing the insulin-producing cells is prepared in vitro (ex vivo) and then introduced, as such, into the patient's body. Encapsulation of insulin-producing cells into a Si-HPMC hydrogel may be performed by mixing or incorporating insulin-producing cells with a viscous solution of Si—HPMC (under the form of a pre-gel); and inducing a decrease in pH using a biological buffer (as described above), which results in crosslinking of Si-HPMC, thereby forming a hydrogel wherein insulin-producing cells are entrapped.

In other embodiments, the final hydrogel containing the insulin-producing cells is produced in vivo (i.e., inside the patient's body). More specifically, the insulin-producing cells are mixed or incorporated in vitro (ex vivo) with a viscous solution of Si-HPMC (under the form of a pre-gel), and the viscous solution is injected into the patient, where, at physiological pH, Si-HPMC undergoes self-reticulation, thereby forming a hydrogel containing insulin-producing cells.

D. Additional Therapeutic Compounds

In certain embodiments, the insulin-producing cells are the only "therapeutically active" ingredient in the Si-HPMC capsule or hydrogel.

In other embodiments, Si-HPMC-encapsulated insulin-producing cells further comprise at least one therapeutic compound.

The therapeutic compound may be an insulin sensitivity enhancer, a glucose absorption inhibitor, a biguanide, an insulin secretion enhancer, an insulin preparation, a glucagon receptor antagonist, an insulin receptor kinase stimulant, a tripeptidyl peptidase II inhibitor, a dipeptidyl peptidase IV inhibitor, a protein tyrosine phosphatase-1B inhibitor, a glycogen phosphorylase inhibitor, a glucose-6-phosphatase inhibitor, a fructose-bisphosphatase inhibitor, a pyruvate dehydrogenase inhibitor, a hepatic gluconeogenesis inhibitor, D-chiroinsitol, a glycogen synthase kinase-3 inhibitor, glucagon-like peptide-1, a glucagon-like peptide-1 analogue, a glucagon-like peptide-1 agonist, amylin, an amylin analogue, an amylin agonist, an aldose reductase inhibitor, an advanced glycation endproducts formation inhibitor, a protein kinase C inhibitor, a γ-aminobutyric acid receptor antagonist, a sodium channel antagonist, a transcript factor NF-κB inhibitor, a lipid peroxidase inhibitor, an N-acetylated-α-linked-acid-dipeptidase inhibitor, insulin-like growth factor-I, platelet-derived growth factor, a platelet-derived growth factor analogue, epidermal growth factor, nerve growth factor, a carnitine derivative, uridine, 5-hydroxy-1-methylhidantoin, EGB-761, bimoclomol, sulodexide, Y-128, a hydroxymethylglutaryl coenzyme A reductase inhibitor, a fibric acid derivative, a β3-adrenoceptor agonist, an acyl-coenzyme A cholesterol acyltransferase inhibitor, probcol, a thyroid hormone receptor agonist, a cholesterol absorption inhibitor, a lipase inhibitor, a microsomal triglyceride transfer protein inhibitor, a lipoxygenase inhibitor, a carnitine palmitoyl-transferase inhibitor, a squalene synthase inhibitor, a low-density lipoprotein receptor enhancer, a nicotinic acid derivative, a bile acid sequestrant, a sodium/bile acid cotransporter inhibitor, a cholesterol ester transfer protein inhibitor, an appetite suppressant, an angiotensin-converting enzyme inhibitor, a neutral endopeptidase inhibitor, an angiotensin II receptor antagonist, an endothelin-converting enzyme inhibitor, an endothelin receptor antagonist, a diuretic agent, a calcium antagonist, a vasodilating antihypertensive agent, a sympathetic blocking agent, a centrally acting antihypertensive agent, an α2-adrenoceptor agonist, an antiplatelets agent, a uric acid synthesis inhibitor, a uricosuric agent a urinary alkalinizer, an oxygen-carrier, or any combination thereof.

II—Uses of Si-HPMC-Encapsulated Insulin-Producing Cells

A. Indications

Si-HPMC-encapsulated insulin-producing cells may be used to treat a patient diagnosed with type 1 diabetes. The patient is preferably a human, and may be a child, a teenager or an adult.

Type 1 diabetes may be diagnosed using any of the methods used clinically to diagnose type 1 diabetes. The World Health Organization defines the diagnostic value of fasting plasma glucose concentration to 7.0 mmol/l (126 mg/dl) and above for diabetes mellitus (whole blood 6.1 mmol/1 or 110 mg/dl), or 2-hour glucose level 11.1 mmol/L or higher (200 mg/dL or higher). Other values suggestive of or indicating diabetes mellitus include elevated arterial pressure 140/90 mm Hg or higher; elevated plasma triglycerides (1.7 mmol/L; 150 mg/dL) and/or low HDL-cholesterol (less than 0.9 mmol/L, 35 mg/dl for men; less than 1.0 mmol/L, 39 mg/dL women); central obesity (males: waist to hip ratio higher than 0.90; females: waist to hip ratio higher than 0.85) and/or body mass index exceeding 30 kg/m$^2$; microalbuminuria, where the urinary albumin excretion rate 20 μg/min or higher, or albumin:creatinine ratio 30 mg/g or higher).

In certain embodiments, the patient has been diagnosed with brittle type 1 diabetes mellitus. The terms "brittle type I diabetes mellitus", "brittle type I diabetes" and "labile type I diabetes" are used herein interchangeably. They refer to a particularly hard to control type 1 diabetes. Almost all diabetic patients experience swings in blood glucose levels, which are larger and less predictable than in non-diabetics. When these swings become intolerable and cause disruption to the patient's life and/or prolonged hospitalization, the person is labeled as having labile or brittle diabetes.

Alternatively, Si-HPMC-encapsulated insulin-producing cells may be used to treat a patient diagnosed with type 1 prediabetes (i.e., before the onset of type 1 diabetes), in particular when glucose tolerance tests show a beginning of deregulation.

B. Administration of Si-HPMC-Encapsulated Insulin-Producing Cells

A method of treatment according to the invention comprises the administration of Si-HPMC-encapsulated insulin-producing cells to a type 1 diabetic patient. The terms "administering", "introducing" and "transplanting" are used herein interchangeably. They refer to the placement of Si-HPMC-encapsulated insulin-producing cells into a subject, by a method or route which results in location of the encapsulated cells at a desired site and where at least a portion of the implanted encapsulated cells remain viable. The period of viability after administration of the patient can be as short as a few hours (e.g., 12 hours, 24 hours) to a few days (e.g., 2 days, 3 days, 5 days, 10 days, 20 days, 30 days or more than 30 days), to as long as several months (e.g., 3 months, 4 months, 5 months, 6 months, 7 months, 8 months, 9 months, 10 months, 11 months, 12 months) or several years (e.g., 2 years, 3 years, 4 years, 5 years or more than 5 years).

Si-HPMC-encapsulated insulin-producing cells may be introduced at any appropriate site of the patient's body. Ideally, the transplantation site should allow rapid vascularization of the tissue in order to keep the ischemia period between transplantation and revascularization as short as possible. Extravascular sites that have been considered as potential islet transplantation sites include, but are not limited to, the pancreas (Stagner et al., Journal of the Pancreas, 2007, 8: 628-636), gastric submucosa (Caiazzo et al., Transplant Proc., 2007, 39: 2620-2623), striated muscle (Svensson et al., Cell Transplant, 2011, 20: 783-788), peritoneums (Fritschy et al., Transplantation, 1991, 52: 777-783), omentum (Ao et al., Transplantation, 1993, 56: 524-529), bone marrow (Cantarelli et al., Blood, 2009, 114: 4566-4574), kidney capsule (Carlsson et al., Transplantation, 2000, 69: 761-766), lymph node (Komori et al., Nature Biotechnol., 2012, 30: 976-983), spleen (Kaufman et al., Transplantation, 1990, 50: 385-391), and a few immuno-privileged sites (Cantarelli et al., Curr. Diab. Rep., 2011, 11: 364-374) such as the anterior eye chamber, the testis, and the thymus).

In certain embodiments of the present invention, Si-HPMC-encapsulated insulin-producing cells are administered by injection subcutaneously to a type 1 diabetes patient. Normoglycemia in diabetic mice and no-human primates has been demonstrated by transplantation of encapsulated islets in subcutaneous tissue (Dufrane et al., Transplantation, 2010, 90: 1054-1062; Kawakami et al., Pancreas, 2001, 23: 375-381; Wang et al., Transplantation, 2002, 73: 122-129; Wang et al., Transplantation, 2003, 76: 29-296). Clinical trials of encapsulated islets transplanted subcutaneously to type 1 diabetics have been reported (Sharp et al., Diabetes, 1994, 43: 1167-1170; and Clinical Islet Transplant Program with Sernova's Cell Pouch).

In certain embodiments of the present invention, Si-HPMC-encapsulated insulin-producing cells are administered intramuscularly to a type 1 diabetes patient. Intramuscular transplantation has already reached the clinical stage in islet autotransplantation (Christoffersson et al., Diabetes, 2010, 59: 2569-2578).

In certain embodiments of the present invention, Si-HPMC-encapsulated insulin-producing cells are implanted into the peritoneal cavity of a type 1 diabetes patient. The term "peritoneal cavity" refers to a space between the parietal peritoneum and visceral peritoneum, which are the two membranes that separate the organs in the abdominal cavity from the abdominal wall. Clinical trials of encapsulated islets transplanted subcutaneously to type 1 diabetics have been reported (Soon-Shiong et al., The Lancet, 1994, 343: 950-951; Scharp et al., Diabetes, 1994, 43: 1167-1170;

Calafiore et al., Diabetes Care, 2006, 29: 137-138; Tuch et al., Diabetes Care, 2009, 32: 1887-1889; and the clinical trials currently performed by Amcyte, Inc., Novocell, Inc. (ViaCyte, Inc.) and Living Cell Technologies (LCT)).

In certain embodiments of the present invention, Si-HPMC-encapsulated insulin-producing cells are implanted into the mesentery of a type 1 diabetes patient. As used herein, the term "mesentery" refers to a fold of membranous tissue that arises from the posterior call of the peritoneal cavity and attaches to the intestinal tract. Normoglycemia in diabetic mice has been demonstrated by transplantation of encapsulated islets in the mesentery (Vernon et al., Cell Transplant, 2012, 21(10): 10.3727/096368912X636786; Rogers et al., Am. J. Pathol., 2010, 177: 854-864).

In certain embodiments of the present invention, Si-HPMC-encapsulated insulin-producing cells are implanted into the omentum of a type 1 diabetic patient, for example into the omemtum adjacent to a branch of the superior mesenteric artery, or into a pouch of the omentum. As used herein, the term "omemtum" refers to a layer of the peritoneum that surrounds abdominal organs. Normoglycemia in diabetic mice has been demonstrated by transplantation of encapsulated islets in the omentum (Kobayashi et al., Cell Transplant, 2006, 15: 359-365).

In certain embodiments of the present invention, Si-HPMC-encapsulated insulin-producing cells are implanted under the kidney capsule of a type 1 diabetic patient. The terms "kidney capsule" and "renal capsule" are used herein interchangeably, and refer to a tough fibrous layer surrounding the kidney and covered in a thick layer of perinephric adipose tissue. Normoglycemia in diabetic mice has been demonstrated by transplantation of encapsulated islets in the renal capsule (Dufrane et al., Transplantation, 2006, 81: 1345-1353).

In certain preferred embodiments, Si-HPMC-encapsulated insulin-producing cells are implanted subcutaneously or intramuscularly. Muscle and subcutaneous tissue exhibit several advantages: they are easy to approach in comparison with other sites such as intraperitoneal organs. Therefore, the encapsulated cells can be easily and transplanted and remove if necessary or desired.

Depending on the site of the patient's body, administration of Si-HPMC-encapsulated insulin-producing cells will be achieved using any of a variety of methods including, but not limited to, by injection, by local infusion, by means of a catheter, by surgical implantation, and the like.

In general, Si-HPMC-encapsulated insulin-producing cells will be administered in a therapeutically effective amount, i.e., an amount that is sufficient to fulfil its intended purpose: that is restoring and/or maintaining euglycemia in a type 1 diabetes patient. The International Islet Transplant Registry has recommended transplants of at least 6,000 islet equivalents per kilogram of recipient body weight to achieve euglycemia. In 2000, the Edmonton Protocol introduced several modifications to the transplantation procedure and recommended transplantation of a mean islet mass of 11,000 islet equivalents per kilogram of recipient body weight. However, it will be apparent to those skilled in the art that the quantity of Si-HPMC-encapsulated insulin-producing cells to be transplanted depends on the ability of the encapsulated cells to provide insulin in vivo in response to glucose stimulation. Thus, the exact amount of Si-HPMC-encapsulated insulin-producing cells to be administered will not only vary from subject to subject, depending on the age, sex, weight, and severity of the blood glucose levels swings suffered by the patient, but also on potency of the Si-HPMC-encapsulated insulin-producing cells, the use (or not) of concomitant therapies (e.g., exogenous insulin therapy) and other clinical factors. These factors are readily determinable by the attending physician in the course of the therapy.

The effects of a treatment according to the invention may be monitored using any of the assays and tests known in the art for the diagnosis of type 1 diabetes, in particular by assessing blood glucose concentration.

C. Combination of Therapies

In certain embodiments, Si-HPMC-encapsulated insulin-producing cells are the only therapeutic agent administered to a type 1 diabetic patient to regulate glycemia. In other embodiments, Si-HPMC-encapsulated insulin-producing cells are used in combination with insulin therapy. The combination allows the administration of a lighter insulin therapy and a better regulation of (hyper and/or hypo) glycemia.

In certain embodiments, Si-HPMC-encapsulated insulin-producing cells are administered in combination with an immunosuppressive treatment. However, in other embodiments, the transplanted type 1 diabetic patient is not administrated a concomitant immunosuppressive treatment.

III—Kits

In another aspect, the present invention provides kits comprising materials useful for carrying out a therapeutic method according to the invention. Materials and reagents for performing a therapeutic method of the present invention may be assembled together in a kit. In certain embodiments, an inventive kit comprises Si—HPMC (for example under the form of a powder or under the form an aqueous solution at pH>12.4), and insulin-producing cells, as well as instructions to encapsulate the insulin-producing cells in Si-HPMC and instructions to administer encapsulated cells to a type 1 diabetic patient or to a type 1 prediabetic patient. In other embodiments, an inventive kit comprises Si-HPMC-encapsulated insulin-producing cells and instructions for administration to a type 1 diabetic patient or to a type 1 prediabetic patient.

Depending on the procedure, the kit may further comprise one or more of: washing buffer and/or reagents, dissolution buffer and/or reagents, gelation buffer and/or reagents, and the like. Protocols for using these buffers and reagents to perform different steps of the procedure may be included in the kit.

The reagents may be supplied in a solid (e.g., lyophilized) or liquid form. The kits of the present invention may optionally comprise different containers (e.g., vial, ampoule, test tube, flask or bottle) for each individual buffer and/or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

A kit according to the present invention may further comprise instructions for using the kit according to a method of the invention. Instructions for using the kit according to a method of the invention may comprise instructions for performing a macroencapsulation, instructions for performing a microencapsulation, instructions for administration/injection/transplantation to a type 1 diabetic patient, and the like.

In certain embodiments, a kit according to the present invention may comprise a device (e.g., a syringe and needle system) for administration of the encapsulated cells to a patient.

Optionally associated with the container(s) can be a notice or package insert in the form prescribed by a governmental agency regulating the manufacture, use or sale of pharmaceutical or biological products, which notice reflects approval by the agency of manufacture, use or sale for human administration.

An identifier, e.g., a bar code, radio frequency, ID tags, etc., may be present in or on the kit. The identifier can be used, for example, to uniquely identify the kit for purposes of quality control, inventory control, tracking movement between workstations, etc.

The invention will be further illustrated by the following figures and examples. However, these examples and figures should not be interpreted in any way as limiting the scope of the present invention.

BRIEF DESCRIPTION OF THE DRAWING

FIG. 1. Kinetics of non-encapsulated neonate pig islets cultivated in Petri dishes for 7 days after isolation. (A) Number of islet equivalent (mean IEQ (islet equivalent quantity)±SEM) calculated as a percentage of IEQ at day 3, day 5 and day 7 by IEQ at day 1 of culture. (B) Insulin specific production (mean qinsulin±SEM) of young porcine islets cultivated for 2 hours in basal medium (black), in 20 mM glucose (grey) or in 20 mM glycose+10 mM theophylline (white) after 1, 3, 5 or 7 days of culture (n=8). * p<0.05.

FIG. 2. Kinetics of neonate pig islets encapsulated in hydrogel for 6 weeks after isolation. (A) Viability staining (Calcein, green, for alive islet and ethidium homodimer, red, for dead islet). (B) Basal insulin specific production (mean qinsulin±SEM) of neonate islets encapsulated in Si-HPMC (black, n=6) or in alginate (grey, n=3). * p<0.05. Si-HPMC sustained neonate pig islet viability and function in culture for at least 42 days—i.e., 6 weeks (max. tested: 72 days).

FIG. 3. Kinetics of pseudo-islet Min6 encapculated in Si-HPMC cultivated in microplate for 9 months. (A) Viability staining (Calcein, green, for alive islet and ethidium homodimer, red, for dead islet) after 1, 3 or 6 months of culture. (B) Basal insulin specific production (mean qinsulin±SEM) (n=3). Ns: no significant differences.

FIG. 4. Insulin production in response to a stimulation. (A) Insulin specific production (qinsulin) of 2 days cultured neonate pig islets encapsulated in Si—HPMC (black circles) or in alginate (black squares) cultivated in basal medium or in 20 mM glucose+10 mM theophylline (G+T). (B) Area under the curve (mean AUC±SEM) of insulin production for 3 hours, including 1 hour of G+T stimulation, of neonate pig islets encapsulated in Si-HPMC (black, n=6) or in alginate (grey, n=3). * p<0.05, ** p<0.005, ns: no significant differences.

FIG. 5. Insulin production of pseudo-islet MIN6 encapsulated in SiHPMC in response to a stimulation. (A) Insulin specific production (qinsulin) in basal medium or in 20 mM glucose+10 mM theophylline (G+T) after 1 month (black circles), 3 months (black squares) and 9 months (black triangles) of culture. (B) Area under the curve (mean AUC±SEM) of insulin production for 3 hours, including 1 hour of G+T stimulation (n=3). Ns: no significant differences.

FIG. 6. Subcutaneous macroencapsulation of MIN6 pseudo-islets (500 IEQ) in Si-HPMC hydrogel transplanted in streptozotocin-induced diabetic (A) NOD NSG immunodeficient mice (STZ high dose, n=4) and (B) immunocompetent C57Bl/6 mice (STZ low dose, n=4). Arrows represent times of graft explantation for concerned mice.

FIG. 7. IL-6 secretion (mean IL-6 quantity±SEM) in the media culture of mouse whole spleen cells or of human macrophages (A) cultivated for 36 hours alone (black, n=4), with Si-HPMC (light grey, n=4) or alginate (dark grey, n=2), and (B) cultivated for 6 hours with LPS (10 ng/mL) (n=4).

FIG. 8. IL-6 secretion (mean IL-6 quantity±SEM) in the media culture of (A) mouse whole spleen cells (n=3) or (B) of human macrophages (n=2) cultivated for 36 hours alone (black) or cocultured with neonate pig islets non-encapsulated (white), encapsulated in Si-HPMC (light grey) or in alginate (dark grey). * p<0.05, ns: no significant differences.

EXAMPLES

Figure 9:
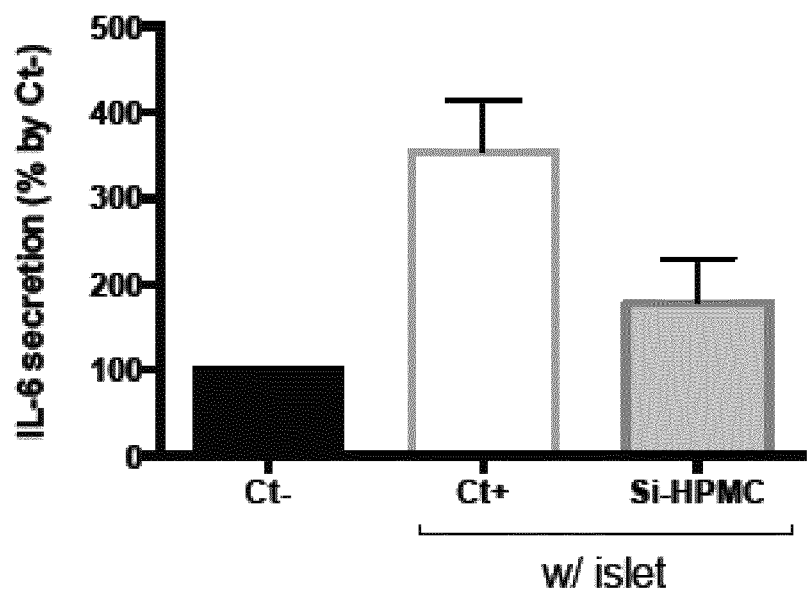
FIG. 9. IL-6 secretion (mean IL-6 percentage/Ct-±SEM) in the media culture of mouse whole spleen cells cultivated for 48 hours alone (Ct-, black) or with transwell co-culture with young porcine islets non-capsulated (white) or encapsulated in Si-HPMC (grey) (n=2).

The following examples describe some of the preferred modes of making and practicing the present invention. However, it should be understood that the examples are for illustrative purposes only and are not meant to limit the scope of the invention. Furthermore, unless the description in an Example is presented in the past tense, the text, like the rest of the specification, is not intended to suggest that experiments were actually performed or data were actually obtained.

Materials and Methods

Ethical

All cares and experiments with animals were carried out in accordance with relevant French guidelines (Décret 2001-464 of May 29, 2001 and Décret 2013-118 of Feb. 1, 2013). Mice were housed in the ONIRIS' Rodent Facility (Agreement Number: 44 266) in a specific pathogen-free environment with sterilized tap water and food. All animal experiments were approved by the Pays de la Loire Regional Committee on the Ethics of Animal Experiments (Approval Number: 01074.01/02). All efforts were made to minimize suffering.

Cells

Neonate Pig Islets (NPIs).

Yucatan neonate pigs were purchased from NRA (Saint Gilles, France). Pancreases were obtained from 1 to 14 days old female or male Yucatan neonate pigs (1 to 2 kg body weight). Piglets were anesthetized with Isofluran and subjected to laparotomy after complete exsanguination. Analgesia of piglets included a premedication with butorphanol and midazolam, and a per-operating morphine chlorhydrate administration. The pancreas was then carefully dissected from surrounding tissue and placed in cooled HBSS supplemented with 10 mM Hepes, 100 U/ml penicillin, and 0.1 mg/ml streptomycin (HBSS buffer). The isolation and culture of neonate pig islets was performed as described by Korbutt et al. (J. Clin. Invest., 1996, 97: 2119-2129). Briefly, pancreases were cut into small pieces of 1 to 2 mm$^3$ using scissors and washed, then digested with 2.5 mg/mL collagenase (Sigma-Aldrich) and gently agitated for 14 to 16 minutes in a shaking water bath at 37° C. The digest was filtered through nylon screen (500 μm) washed four times in HBSS supplemented with 10 mM Hepes, 100 U/ml penicillin, 0.1 mg/ml streptomycin and 0.5% BSA, and then placed into petri dishes non cell culture treated (Dutscher) containing Ham's F10 (Dutscher) supplemented with 10 mM glucose (Sigma-Aldrich), 50 mM IBMX (Sigma-Aldrich), 5 g/L BSA (Sigma-Aldrich), 2 mM L-glutamine (Dutsher), 10 mM nicotinamide (Sigma-Aldrich), 100 IU/ml penicillin and 100 mg/ml streptomycin (Dutsher). Culture dishes were maintained at 37° C. in humidified air (5% $CO_2$, 95% air), with the medium changed the first day after isolation and every other day thereafter. Once encapsulated within hydrogels (see below), NPIs were cultured in Ham's F10 supplemented with 10 mM glucose, 50 mM IBMX, 2 mM l-glutamine, 10 mM nicotinamide, 100 U/ml penicillin, 100 mg/ml streptomycin and 10% porcine serum.

MIN6 Pseudoislets (PIs).

MIN6 murine insuline cells were kindly provided by Pr. Jun-ichi Miyazaki (Osaka University Medical School, Japan). Low passage (5-10) MIN6 cells were chosen to form PIs. MIN6 cells were cultured in Dulbecco's Modified Eagle's Medium (DMEM, Dutsher) containing 25 mM glucose and supplemented with 10% heat-inactivated bovine serum (Invitrogen, Carlsbad, USA), 1% penicillin/streptomycin/neomycin mixture (PAA) and 50 μM mercaptophenol (Sigma-Aldrich). MIN6 PIs were prepared by seeding $10^6$ cells/mL in 50 mL chamber RCCS bioreactor (Synthecon, Houston, USA) for 4 days and 3 days in non-treated petri dishes at 37° C. in humidified air (5% $CO_2$, 95% air).

Islet Equivalent Numeration.

Islets equivalent quantities were determined to standardize the number of islets in relation to their volume. One IEQ is equal to an islet of 150 μm diameter according to the criterion set at the Second Congress of the International Pancreas and Islet Transplantation Association (Ricordi et al., Acta Diabetol. Lat., 1990, 27: 185-195). For each counting, three samples of 50 μL were used.

Macroencapsulation of NPIs and PIs in Si-HPMC and Alginate Hydrogels

Islet concentration in macrocapsules was targeted at 2500 islet equivalents (IEQ)/mL. 3% (w/v) silanized hydroxypropyl methylcellulose (Si-HPMC) was provided by LIOAD (Laboratoire d'Ingénierie Ostéo-Articulaire et Dentaire—UMR_S 791, Nantes, France). Si-HPMC and acid buffer were mixed using two syringes linked by a luer lock in a 2:1 (v:v) ratio, respectively to achieve a final 2% (w/v) hydrogel (Bourges et al., Adv. Colloid Interface Sci., 2002, 99: 215-228). After 10 minutes of gelation (pre-gel), islets (in a volume of 20 μL) were dropped inside 200 μL of the hydrogel by using a tapered 0-200 μL cone. Islets were then embedded within the hydrogel by extrusion through a 23 gauge needle. 200 μL of the gel and islet mix were placed in 48-well TCPS plates to obtain in vitro Si-HPMC islet macrocapsules. Growing media was added following 60 minutes of incubation at 37° C.

Alginate macrocapsules were produced using a clinical grade low viscosity and high glucuronate sodium alginate (PRONOVA UP LVG) from Novamatrix (Sandvika, Norway). Sodium alginate was solubilized in 0.9% NaCl (w/v; Sigma-Aldrich) at 2.2% (w/v) by gentle stirring overnight at 4° C. and then sterilized using a 0.2 μM filtration (Millipore, Darmstadt, Germany). NPIs and PIs were washed three times in 0.9% NaCl, and suspended in calcium alginate 2.2% solution in 1:8 (v:v) ratio. Macrospheres were obtained by extrusion through a 23 gauge needle using a syringe driver, into a 100 mM $CaCl_2$ (Sigma-Aldrich) gelation bath for 10 minutes. Macrospheres were then sequentially washed in two 0.9% NaCl 10 minutes baths and in culture media. The average macrosphere obtained was 2 mm in diameter. Macrocapsules were obtained by dropping 200 μL of the gel and islet mix in 48-well plates followed by a 20 minute incubation with a 100 mM $CaCl_2$ solution surrounding and covering the capsule. After gelling, $CaCl_2$ was removed and the macrocapsules were sequentially washed in 0.9% NaCl (two 20 minutes baths) and in medium.

Encapsulated NPIs or PIs were maintained at 37° C. in humidified air (5% $CO_2$, 95% air) and the culture medium was changed every 2 to 3 days.

NPIs and PIs Viability In Vitro

Viability of encapsulated or un-encapsulated NPIs and PIs was assessed using the LIVE/DEAD kit (Calcein AM and Ethidium bromide (EthD-1)) according to the manufacturer recommendations (Life Technologies, Carlsbad, USA). Before being tested, un-encapsulated cells were washed once in D-PBS (Sigma Aldrich) and encapsulated cells were washed three times 15 minutes in D-PBS. EthD-1 and calcein AM probes were incubated for 30 to 60 minutes at a concentration of 4 μM and 2 μM, respectively.

NPIs and PIs Function In Vitro

Glucose-Stimulation Insulin Secretion (GSIR).

The capacity of un-encapsulated or encapsulated islets to release insulin in response to acute glucose±theophylline (a potentiator of insulin secretion) was assessed by static or static/dynamic methods respectively. Basal medium (B) was composed of RPMI (PAA) supplemented with 2.8 mM glucose (PAA), 2 mM L-glutamine and 5 g/L BSA (Sigma-Aldrich). Glucose stimulated medium (G) and glucose plus theophylline medium (G+T) were basal medium supplemented with 20 mM glucose and 20 mM glucose±10 mM theophylline (Sigma-Aldrich), respectively. As described by Korbutt et al. (J. Clin. Invest., 1996, 97: 2119-2129), static GSIR of un-encapsulated islets was assessed by incubating 50 islets equivalent (IEQ) (previously washed in basal medium) for 2 hours in B, G or G+T media. Tissue and medium were then separated by centrifugation and assayed for their respective insulin content. A static/dynamic method was used to assess GSIR of encapsulated islets (500 IEQ/200 μL of hydrogel). First, encapsulated islets were washed 5 sequential incubations in basal medium for 30 minutes. Then, basal and stimulated productions of insulin were assessed by sequentially incubating encapsulated islets for 30 minutes in 400 μL of basal medium (2 times), glucose plus theophylline (2 times) and basal medium (3 times).

Basal Insulin Secretion of Encapsulated Islets in Culture.

Each week, supernatant of culture medium was collected from encapsulated islets 24 hours after the last medium change to assay for insulin basal production by encapsulated islets in culture.

Insulin Assay and Results Calculation.

Insulin was assayed by ELISA (Mercodia, Uppsala, Sweeden). The specific production rate (q) of insulin (ins) was calculated using the following equation were X is the number of IEQs and t is the time of production:

$$q_{ins} = \left(\frac{1}{X}\right)\left(\frac{dIns}{dt}\right) \text{ (expressed in pg/1000 IEQ/h)}$$

Immune Biocompatibility and Immunoprotection of Hydrogel

Islet Incubation with Murine Splenocytes and Human Macrophages.

Un-encapsulated or encapsulated islets were co-cultured with human macrophages or murine splenocytes. Human monocytes were purchased from CIC (Centre d'Investigation Clinique, Nantes, France). Human macrophages were obtained by in vitro differentiation of monocytes cultured for 6 days in petri dishes ($10^6$ cells/cm$^2$) in RPMI 1640 supplemented with 10% FCS (v/v), 2 mM glutamine, 100 IU/mL penicillin, 100 mg/mL streptomycin and $10^4$ U/mL of rhM-CSF (recombinant macrophagescolony stimulating factor, R&D Systems, Abingdon, UK). Macrophages were taken off by accutase (Sigma-Aldrich) and plated at $4\times10^4$ cells per well in 48-well plates in 500 μL of complete medium. Splenocytes were isolated from NOD/ShiLTJ mice by gentle mechanical disruption of the spleen, passing through a 70 μm sieve, followed by lysis of the red blood cells. For cytokine secretion assays, splenocytes were plated at $2\times10^5$ cells per well in 48-well plate or at $4\times10^5$ cells per well in 24-well plate in 500 or 1000 μL of RPMI 1640 medium supplemented with 10% FCS, 2 mM L-glutamine and 100 IU/mL penicillin, 100 mg/mL streptomycin, respectively.

Cytokines Secretion.

All media were collected after 40±2 hours and stored at a temperature of −20° C. A CBA test (Becton Dickinson, Franklin Lakes, USA) or an ELISA test (Bio-techne, Menneapolis, USA) was performed for TNF α, IFN γ, IL-1 β, IL-6, IL-12 or IL-10 quantification (FACS Aria, BD Bioscience).

Transplantation of Encapsulated MIN6 Pseudoislet (PIs) in Streptozotocin-Induced Diabetes Immunodeficient NSG and Immunocompetent C57Bl/6 Mice.

Female mice were used between 6 to 12 weeks of age. NOD scid gamma immunodeficient (NSG) mice were purchased from Charles River Laboratories (Lyon, France). Fasting mice were rendered diabetic by a single intraperitoneal injection of a high dose of 150 mg/kg body weight streptozotocine (Sigma Aldrich; freshly dissolved in citrate buffer) 5 days before transplantation. C57Bl/6 mice were obtained from Janvier Labs (Le Genest Saint Isle, France). C57Bl/6 mice were rendered diabetic by five intraperitoneal injections (once a day) of low doses of 50 mg/kg body weight streptozotocine (Sigma Aldrich; freshly dissolved in citrate buffer) 40 days before transplantation. Glycaemia was monitored using a Glucotrend/Accu-Check (Roche Diagnostics, Mannheim, Germany). Blood samples were obtained from the tail vein. Diabetes was diagnosed when glycaemia was higher than 13.5 mmol/L for two consecutive monitorings. On the day of the injection, the recipient animals were anesthetized using Isofluran. 500 IEQs were encapsulated in 200 μL Si-HPMC hydrogel, as described above. After 10 minutes of pre-gelling, Si-HPMC-encapsulated islets were subcutaneously injected to the right flank of anesthetized mice. Macrocapsules of SiHPMC were then removed from some mice. For that, mice are anesthetized with Isofluran and analgesia was performed with Buprenorphin.

Statistical Analysis.

Data are expressed as means±SEM of independent observations. Statistical analyses were performed using Prism (GraphPad Software, Inc.) and statistical tests indicated in figure legends.

Results

While the absence of encapsulation is characterized by a fast decrease in the viability of neonate pig islets cultured in vitro (see FIG. 1(A)), Si-HPMC encapsulation allows survival of the neonate pig islets for more than 42 days (see FIG. 2(A), max. tested: 72 days). The same result was also observed for murine pancreatic pseudo-islets (Minh) for up to 9 months of in vitro culture (see FIG. 3(A)).

As far as the in vitro functionality of encapsulated islets is concerned: the basal quantity of insulin secreted in vitro by neonate pig islets was found to be higher when encapsulated in Si-HPMC than when encapsulated in alginate (clinical grade GMP Novamatrix) (see FIG. 2(B), p<0.05). The in vitro insulin-secretion of neonate pig islets was not stimulated by glucose (see FIG. 1(B)). This result was expected as it is known that neonate pig islets are functionally immature. However, as expected (Korbutt et al., J. Clin. Invest., 1996, 97: 2119-2129), the in vitro insulin-secretion of neonate pig islets was observed to be stimulated by glucose in combination with theophylline, a potentializing agent (see FIG. 1(B), p<0.05). Delays in the diffusion of stimulating agents (glucose+theophylline) and of insulin itself through hydrogels like alginate make the insulin-secretion stimulation tests more difficult. In order to solve this technical problem, which is inherent to encapsulation, the present Inventors have developed 'dynamic' tests of immune-secretion (FIG. 4(A)). If the quantity of insulin secreted after stimulation with glucose and theophylline was found to be higher (p<0.05) with alginate than with Si-HPMC at the beginning of the culture, the reverse is true afterwards (see FIG. 4(B)). In the case of murine pseudo-islets, the basal insulin-secretion (much higher in quantity) was found to be maintained for the whole in vitro culture after encapsulation with Si-HPMC (see FIG. 3(B), max tested: 9 months). The same was true for stimulated insulin-secretion (see FIG. 5).

The ability of Si-HPMC to self-reticulate (or self-cross) at physiological pH and temperature allows its subcutaneous injection prior to polymerization using a simple syringe and needle system (23 G×1). Using such administration route, the present Inventors have shown that murine pancreatic pseudo-islets encapsulated in Si-HPMC can treat streptozotocin (STZ)-induced diabetes in immunodeficient NOD mice (see FIG. 6(A)) and in immunocompetent C57Bl/6 mice (see FIG. 6(B)). The high dose injection of STZ was found to chemically destroy all the insulin-producing cells in the pancreas. In contrast, repeated injections of low doses of STZ resulted in a partial and limited chemical destruction of insulin-producing cells in the pancreas, leading to autoimmune diabetes through the release of auto-antigens by insulin cells (Weide et al., Diabetes, 1991, 40: 1157-1162; Rossini et al., Proc. Natl. Acad. Sci. USA, 1977, 74: 2485-2489). The surgical removal of the hydrogel containing the pancreatic pseudo-islets leads a fast increase in glycemia, indicating that diabetes correction is indeed due to the macro-encapsulated islets rather than to other factors (such as regeneration of insulin-producing cells in the pancreas or action of pseudo-islets or MING cells escaped from the subcutaneous hydrogel).

In order to test the bio-immune-compatibility of Si-HPMC as a bio-artificial pancreas, the present Inventors have assessed the secretion of IL-6, a pro-inflammatory cytokine secreted by macrophages and dendritic cells. In contrast to alginate which itself induces IL-6 secretion by human macrophages and murine splenocytes, Si—HPMC was found to have no effect on the induction of 11-6 secretion (see FIG. 7(A)). LPS was used as a positive control allowing assessment of the functionality of the cells tested (see FIG. 7(B)).

Si-HPMC was found to protect islets from being recognized by cells of the immune system, thus conferring to the encapsulated islets an efficient immunoprotection. Indeed, as shown by FIG. 8, Si-HPMC prevents in vitro secretion, by human macrophages and by murine splenocytes, of IL-6 induced by contact with pig islets. In contrast, alginate has itself the ability to induce IL-6 secretion (see above). Moreover, Si-HPMC limits IL-6 secretion by immune cells of induced by the release of soluble factors by encapsulated islets (co-culture tests in transwell, see FIG. 9).

Long term durability and efficacy of Si-HPMC encapsulation of insulin-producing cells have not yet been validated. All the experiments reported above have been performed using a standard formulation containing a final concentration of 2% (w/v) of Si-HPMC to prepare the hydrogel). As will be recognized by one skilled in the art, the final concentration of Si-HPMC can be modified and optimized to find the best compromise between diffusion, viability, stability and durability. Lower concentration of Si-HPMC (e.g. about 1.5%, about 1%, or about 0.5%) and higher concentrations of Si-HPMC (e.g., about 2.5%, about 3%, about 4% or about 5% can be used to modulate the density of the hydrogel and therefore its durability while still allowing the diffusion of insulin and glucose and maintaining viability.

What is claimed is:

1. A method for treating type 1 diabetes in a patient, in particular for restoring and/or maintaining euglycemia in a type 1 diabetic patient or a type 1 prediabetic patient, said method comprising a step of administering to said patient a therapeutically effective amount of Si-HPMC-encapsulated insulin-producing cells, wherein the insulin-producing cells are macro-encapsulated in Si-HPMC flat-sheet membranes or in Si-HPMC hollow fiber membranes or wherein the insulin-producing cells are micro-encapsulated.

2. The method according to claim 1, wherein Si-HPMC has the following simplified formula:

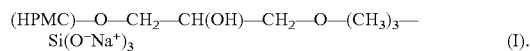

(HPMC)—O—CH$_2$—CH(OH)—CH$_2$—O—(CH$_3$)$_3$—Si(O$^-$Na$^+$)$_3$     (I).

3. The method according to claim 1, wherein the insulin-producing cells are isolated allogenic pancreatic islets or isolated xenogenic pancreatic islets.

4. The method according to claim 1, wherein the insulin-producing cells are isolated cells selected from the group consisting of pancreatic β-cells, pancreatic β-like cells, and any combination thereof.

5. The method according to claim 4, wherein pancreatic β-like cells are obtained by differentiation of embryonic stem cells, induced pluripotent stem cells, multipotent mesenchymal stromal cells, ductal cells, hepatocytes, or β-cells.

6. The method according to claim 1, wherein the insulin-producing cells are micro-encapsulated into Si-HPMC microbeads, Si-HPMC microspheres, or Si-HPMC microcapsules.

7. The method according to claim 1, wherein the insulin-producing cells are encapsulated in Si-HPMC with at least one therapeutic compound.

8. The method according to claim 1, wherein the type 1 diabetes patient suffers from brittle diabetes.

9. The method according to claim 1, wherein the Si-HPMC-encapsulated insulin-producing cells are administered by subcutaneous injection, by intramuscular injection, or by implantation in the peritoneal cavity, in the mesentery, in the omemtum, or in the renal capsule.

* * * * *